US008236945B2

(12) United States Patent
Decout et al.

(10) Patent No.: US 8,236,945 B2
(45) Date of Patent: *Aug. 7, 2012

(54) PROCESS FOR PREPARING DISULFIDES AND THIOSULPHINATES AND COMPOUNDS PREPARED

(75) Inventors: Jean-Luc Decout, Vaulnaveys le Haut (FR); Beatrice Gerland, Valence (FR); Jerome Desire, Tencin (FR)

(73) Assignee: Universite Joseph Fourier (Grenoble1) (FR)

( * ) Notice: Subject to any disclaimer, the term of this patent is extended or adjusted under 35 U.S.C. 154(b) by 649 days.

This patent is subject to a terminal disclaimer.

(21) Appl. No.: 12/298,156

(22) PCT Filed: Apr. 24, 2007

(86) PCT No.: PCT/FR2007/000691
§ 371 (c)(1),
(2), (4) Date: Feb. 2, 2009

(87) PCT Pub. No.: WO2007/122333
PCT Pub. Date: Nov. 1, 2007

(65) Prior Publication Data
US 2009/0264637 A1 Oct. 22, 2009

(30) Foreign Application Priority Data

Apr. 24, 2006 (FR) .................................. 06 03614
Oct. 27, 2006 (FR) .................................. 06 09460

(51) Int. Cl.
*A61K 31/7068* (2006.01)
*A61K 31/7072* (2006.01)
*C07H 19/06* (2006.01)
*C07H 19/067* (2006.01)
*C07H 19/073* (2006.01)

(52) U.S. Cl. ............... 536/28.5; 536/28.52; 536/28.53; 536/28.54; 536/28.55; 514/49

(58) Field of Classification Search ......................... None
See application file for complete search history.

(56) References Cited

U.S. PATENT DOCUMENTS

2010/0075917 A1* 3/2010 Decout et al. ................ 514/50

FOREIGN PATENT DOCUMENTS

| EP | 0 348 170 | 12/1989 |
| EP | 0 963 995 | 12/1999 |
| JP | 62283982 | 12/1987 |
| WO | 03/002577 | 1/2003 |

OTHER PUBLICATIONS

Yuzhakov et al., "3'-Mercapto-2',3'-dideoxynucleotides are high effective terminators of DNA synthesis catalyzed by HIV reverse transcriptase" FEBS Letters (1992) vol. 306 No. 2-3, pp. 185-188.*

Divakar et al., "Approaches to the Synthesis of 2'-Thio Analogues of Pyrimidine Ribosides" J. Chem. Soc. Perkin Transactions 1 (1990) pp. 969-974.*
Dueholm et al., "Convergent Synthesis of 2',3'-Dideoxy-3'-methylthio and 2',3'-Dideoxy-3'-mercapto Nucleosides and their Disulfide Analogues—Potential Anti-HIV Agents" Montashefte fur Chemie (1993) 124, 37-53.*
Raines et al., "Enzymatic incorporation of 29-thio-CTP into the HDV ribozyme" RNA (1998) vol. 4 pp. 340-345.*
Roy et al., "Thionucleotides as Inhibitors of Ribonucleotide Reductase" Nucleosides, Nucleotides, and Nucleic Acids (2003) vol. 23 No. 5-8, pp. 883-885.*
Liu et al., "Preparation and cleavage reactions of 3'-thiouridyl1-(3'→5')-uridine" J. Chem Soc. Perkin Trans. 1 (2000) pp. 2227-2236.*
Hitoshi Kuniyasu, et al.; "Palladium-Catalyzed Addition and Carbonylative Addition of Diaryl Disulfides and diselenides to Terminal Acetylenes"; Journal of the American Chemical Society 1991; 113; pp. 9796-9803.
Franklin A. Davis, et al.; "Chemistry of the Sulfur-Nitrogen Bond. 12 Metal-Assisted Synthesis of Sulfenamide Derivatives from Aliphatic and Aromatic Disulfides"; Journal of Organic Chemistry 1977; vol. 42; No. 6; pp. 967-972.
Laurent Bischoff, et al.; 2,4-Dinitrophenyl 4-Methoxybenzyl Disulfide: A New Efficient Reagent for the Electrophilic Sulfenylation of β-Amino Ester Enolates; Journal of Organic Chemistry 1997; 62; pp. 4848-4850.
Ruoyu Xiao, et al.; "Catalysis of Thio/Disulfide Exchange—Glutaredoxin 1 and Protein-Disulfide Isomerase use Different Mechanisms to Enhance Oxidase and Reductase Activities"; Journal of Biological Chemistry 2005; vol. 280; No. 22; Issue of Jun. 3; pp. 21099-21106.
Eric Block; "The Organosulfur Chemistry of the Genus Allium—Implications for the Organic Chemistry of Sulfur"; Angew. Chem. Int. Ed. Engl. 1992, 31, pp. 1135-1178.

(Continued)

*Primary Examiner* — Eric S Olson
(74) *Attorney, Agent, or Firm* — Cantor Colburn LLP

(57) ABSTRACT

Process for preparing a compound of the formula (I) R1-S(O)$_x$—S(O)$_y$R2 in which R1 represents a molecular hydrocarbon radical which can be substituted and/or interrupted by one or more atoms and/or by one or more groups containing one or more atoms, said atoms being selected from N, O, P, S, Si and X, where X represents a halogen; R2, independently of R1, represents a carbon-containing group or a molecular hydrocarbon radical which can be substituted and/or interrupted by one or more atoms and/or by one or more groups containing one or more atoms, said atoms being selected from N, O, P, S, Si and X, where X represents a halogen, and x and y are selected from 0 and 1 in such a way that the sum of x and y is not more than 1, characterized in that a compound of formula (II) R1-S(O)$_x$—R3-Si(R4)(R5)(R6) in which R3 represents a hydrocarbon chain of two carbon atoms, which is optionally unsaturated and/or substituted, and R4, R5 and R6, which are identical or different, each represent, independently of one another, a hydrocarbon group, is reacted with a compound of formula (VII) R2-S(O)$_y$—X in which X represents a halogen, intermediate compounds, and compounds prepared.

10 Claims, No Drawings

OTHER PUBLICATIONS

R. Kharrat, et al.: "Maurotoxin, a four disulfide bridge toxin from Scorpio maurus venom: purification, structure and action on potassium channels"; FEBS Letters 1997; 406; pp. 284-290.

Eun Kyoung Ryu, et al.; "Synthesis of radioiodine labeled dibenzyl disulfide for evaluation of tumor cell uptake"; Bioorganic & Medicinal Chemistry 2004; 12; pp. 859-864.

Vivekananda M. Vrudhula, et al.; "Reductively Activated Disulfide Prodrugs of Paclitaxel"; Bioorganic & Medical Chemistry Letters 2002; 12; pp. 3591-3594.

Changnian Liu, et al.; "Eradication of large colon tumor xenografts by targeted delivery of maytansinoids"; Proc. Natl. Acad. Sci. USA; Aug. 1996; vol. 93; pp. 8618-8623.

Stephane Chambert, et al.; "Recent Developments in the Synthesis, Chemical Modifications and Biological Applications of Sulfur Modified Nucleosides, Nucleotides and Oligonucleotides"; Organic Preparations and Procedures International 2002; vol. 34; pp. 26-85.

Beatrice Roy, et al.; "Deoxyribonucleoside 2'- or 3'-Mixed Disulfides: Prodrugs to Target Ribonucleotide Reductase and/or to Inhibit HIV Reverse Transcription"; J. Med. Chem. 2003; 46; pp. 2565-2568.

Ming Bao, et al.; "N-Trifluoroacetyl Arenesulfenamides, Effective Precursors for Synthesis of Unsymmetrical Disulfides and Sulfenamides"; Tetrahedron 2003; 59; pp. 9655-9659.

Catherine Leriverend, et al.; "A New Mild Synthesis of Unsymmetrical Disulfides by Reaction of Dithioperoxyesters with Thiols"; Synthesis—Short Papers 1994; pp. 761-762.

Stanley J. Brois, et al.; "A New Pathway to Unsymmetrical Disulfides. The Thiol-Induced Fragmentation of Sulfenyl Thiocarbonates"; Journal of the American Chemical Society; 1970; 92; pp. 7629-7631.

Teruaki Mukaiyama, et al.; "A Convenient method for the Preparation of Unsymmetrical Disulfides by the use of Diethyl Azodicarboxylate"; Tetrahedron Letters 1968; No. 56; pp. 5907-5908.

Rei Matsueda, et al.; "3-Nitro-2-Pyridinesulfenyl Group for Protection and Activation of the Thiol Function of Cysteine"; Chemistry Letters 1981; pp. 737-740.

D.H.R. Barton, et al.; "A New Procedure for the Conversion of Thiols into Reactive Sulfenylating Agents"; J. Org. Chem. 1991; 56; pp. 6697-6702.

Engelbert Kuhle; "One Hundred Years of Sulfenic Acid Chemistry—I. Sulfenyl Halide Syntheses"; International Journal of Methods in Synthetic Organic Chemistry, Synthesis-Reviews 1970; No. 11; pp. 561-580.

Engelbert Kuhle; "One Hundred Years of Sulfenic Acid Chemistry—IIa. Oxidation, Reduction, and Addition Reactions of Sulfenyl Halides"; Synthesis-Reviews 1971; pp. 563-586.

M.B. Anderson, et al.; "Nucleophilic and Electrophilic Mercaptanylations via 2-(Trimethylsilyl)ethanethiol-Derived Reagents"; J. Org. Chem. 1988; 53; pp. 3125-3127.

Walter Stamm; "Organosilicon and Tin Alkylthiols"; J. Org. Chem 1963; vol. 28; pp. 3264-3266.

Anu Mahadevan, et al.; "Silver Fluoroborate Promoted Sulfur Alkylation of β-Silyl Ethyl Sulfides. Selective Synthesis of β-Thioglycosides"; Snythetic Communications 1994; pp. 3099-3107.

Stefano Colonna, et al.; "Enantioselective Synthesis of Thiosulfinates and of Acyclic Alkylidenemethylene Sulfide Sulfoxides"; Eur. J. Org. Chem. 2005; pp. 1727-1730.

Samuel Braverman, et al.; "A Convenient Preparation of Mixed Allylic and Allenic Thiosulfinates"; Tetrahedron Letters 2004; 45; pp. 8235-8238.

Tom J. Maricich, et al.; "Reaction of Benzenesulfinyl Azide with Thiols and Amines. Preparation of Thiosulfinates and Sulfinamides"; J. Org. Chem. 1984; 49; pp. 1931-1934.

Mitchell D. Refvik, et al.; "The Reactions of a 1-Alkenesulfenate Anion with TMS-X Reagents; a Variable Temperature NMR Study"; Can. J. Chem. 1998; 76; pp. 213-220.

Sylvie M. Lacombe; "Oxysulfur Compounds Derived from Disulfides: Stability and Reactivity"; Reviews on Heteroatom Chemistry 1999; vol. 21 pp. 1-41.

Guangcheng Lui, et al.; "Catalytic Asymmetric Synthesis of tert-Butanesulfinamide. Application to the Asymmetric Synthesis of Amines"; J. Am. Chem. Soc. 1997; 119; pp. 9913-9914.

B.B. Whitmore, et al.; "Thiosulfinates"; Natural Food Antimicrobial Systems 2000; pp. 349-379.

Richard Johnson, et al.; "Lability of Glycosidic Linkages of 2'-Thioribonucleosides"; Tetrahedron 1995; vol. 51; No. 17; pp. 5093-5098.

Block, Eric et al.: "The chemistry of alkyl thiosulfinate esters. 9. Serendipitious synthesis of alkyl. trimethylsilydithioformates by trapping of bis(trimethylsilyl)thione with alkanesulfenic acids. Synthesis of bis- and tris (trimethylsily)methanethiols" Tetrahedron Letters, vol. 26, No. 19, 1985, pp. 2259-2262 XP002457390.

Brzezinska, Ewa et al: "Disulfides 1. Syntheses Using 2,2'-Dithiobis(benzothiazole)" Journal of Organic Chemistry, vol. 59, No. 26, 1994, pp. 8239-8244, XP002417956.

Chambert, Stephane et al.: "The 2-(trimethylsilyl) ethyl sulfur group in synthesis" Synthesis, vol. 16, 2002, pp. 2319-2334, XP002447017.

Chambert, Stephane et al: "2-Trimethylsilylethyl Sulfides in the von Braun Cyanogen Bromide Reaction: Selective Preparation of Thiocyanates and Application to Nucleoside Chemistry" Journal of Organic Chemistry, vol. 67, No. 6, 2002, pp. 1898-1904, XP002417828.

Chambert, Stephane, et al.: "2-(trimethylsilyl) ethanethiol in Nucleoside Chemistry. A Short Route for Preparing Thionucleosides and Their Methyl Disulfides" Journal of Organic Chemistry, vol. 65, No. 1, 2000, pp. 249-253, XP002417827.

Ferritto, Rafael et al: "Photoreductive cleavage of phenyl-selenium bonds of phenylselenoalkanes" Tetrahedron Letters, vol. 35, No. 8, 1994, pp. 1193-1196, XP002457391.

Higson, Adrian P., et al. "Synthesis and structure of S- nucleosidyl S-aryl disulfides and their reaction with phosphites" Tetrahedron, vol. 52, No. 3, 1996, pp. 1027-1034, XP002417962.

Kim, Yong Hae, et al.: "New selective oxidation of unsymmetrical thiolsulfinates to the corresponding thiolsulfonates with sodium metaperiodate" Tetrahedron Letters, vol. 26, 1978, pp. 2305-2308, XP002417961.

Miller, Naishun, et al: "Nucleosides XXI, Synthesis of some 3'-substituted 2', 3' dideoxyribonucleosides of thymine and 5-methylcytosine" Journal of Organic Chemistry, vol. 29, No. 7, 1964, pp. 1772-1776, XP002417958.

Sun, Sengen, et al: "Synthesis of 3'-thioribonucleosides and their incorporation into oligoribonucleotides via phosphoramidite chemistry" XP002418097 extrait de STN; Database accession No. 1997:743633 *abrege* & RNA, 3 (11), 1352-1363 CODEN: RNARFU; ISSN: 1355-8382, 1997.

Sun, Sengen, et al.: "Synthesis of 3'-thioribonucleosides and their incorporation into oligoribonucleotides via phosphoramidite chemistry" RNA, vol. 3, No. 11, 1997, pp. 1352-1363, XP002337182, figure 1.

Wempen, Iris et al. "Nucleosides LV. Synthesis of a sulfur-bridged thymine anhydronucleoside and derivatives" Journal of Organic Chemistry, vol. 34, No. 4, 1969, pp. 1020-1025, XP002417960.

* cited by examiner

PROCESS FOR PREPARING DISULFIDES AND THIOSULPHINATES AND COMPOUNDS PREPARED

CROSS REFERENCE TO RELATED APPLICATION

This application is a 371 of international application PCT/FR2007/000691, filed 24 Apr. 2007 which claims priority from French application no. 06/03614, filed 24 Apr. 2006 and French application no. 06/09460, filed 27 Oct. 2006.

The present invention relates to the preparation of mixed and symmetrical disulfide compounds and indirectly, after easy reduction of these disulfides, to the preparation of the corresponding thiols. It also relates, according to the same principle, to the preparation of thiosulfinates and in particular asymmetrical thiosulfinates.

Disulfides are important reaction intermediates in organic synthesis. They can, for example, be used as reactants in the context of additions catalyzed by palladium (Kuniyasu et al., *J. Am. Chem. Soc.*, 1991, 113, 9796), give access in the presence of mercury salts to sulfenamides (Davis et al., *J. Org. Chem.*, 1977, 42, 967) or can also be used for the electrophilic sulfenylation of enolates (Bischoff et al., *J. Org. Chem.*, 1997, 62, 4848).

Moreover, the reversible disulfide-thiol redox transformation plays a central role in the regulation of many physiological systems, in particular in proteins (Xiao et al., *J. Biol. Chem.*, 2005, 280, 21099). Many molecules comprising one or more disulfide functional groups thus exhibit highly advantageous biological activities: for example, garlic acid has anticancer properties (Block, E., *Angew. Chem. Int. Ed.*, 1992, 31, 1135) and maurotoxin acts on $K^+$ membrane ion channels (Kharrat et al., *FEBS Letters*, 1997, 284).

Furthermore, the ability of the disulfides to be easily reduced within the cell makes the S—S bond a connection much used in the context of a "prodrug" approach (Kyung Ryu et al., *Biorg. Med. Chem.*, 2004, 12, 859; Vrudhula et al., *Bioorg. Med. Chem. Lett.*, 2002, 12, 3591). It makes it possible to combine a bioactive group with a vector which allows a target to be reached, it being possible for the two partners to be subsequently separated by in vivo reduction of the disulfide functional group (for example, Liu et al., *Proc. Natl. Acad. Sci. USA.*, 1996, 93, 8618).

Thiol functional groups and disulfide functional groups have major applications in chemistry and in biology.

Thus, they are advantageous in peptide synthesis and the synthesis of conjugated peptides.

They are particularly important in the field of nucleic acids, as illustrated in the review article by Chambert and Décout (Org. Prep. Proc. Int., 2002, 34, 27-85).

Thus, the recent development of thionucleosides as analogs of substrates of enzymes involved in the biosynthesis of nucleic acids having antiviral and/or antitumor biological properties has demonstrated the importance of the introduction of a mixed disulfide functional group onto a nucleoside. The thiol functional group, protected in the form of a methyl disulfide, can thus be reduced in vivo to give the active form of the nucleoside. This "prodrug" approach of in situ release makes it possible to avoid the decomposition of the free thiol, which is not very stable (rapid oxidation in air to give symmetrical disulfide and/or intramolecular decomposition by deglycosylation) (B. Roy et al., *J. Med. Chem.*, 2003, 46, 2565). The nucleoside in its active form can subsequently interact after phosphorylation with the target enzymes.

While the synthesis of symmetrical disulfides can be carried out simply by oxidative coupling of two molecules of the same thiol, the preparation of mixed disulfides remains more difficult in organic synthesis due to the production of a mixture comprising the symmetrical disulfides. Generally, a sulfenylating agent reacts with a first thiol, to be subsequently displaced by nucleophilic substitution by a second thiol in order to obtain the desired disulfide. Numerous synthetic routes can then be envisaged due to the great variety of possible sulfenylating agents.

The latter can be of the following types: N-trifluoroacetylarenesulfenamides (Bao et al., *Tetrahedron*, 2003, 9655), dithioperoxyesters (Lerévérend et al., *Synthesis*, 1994, 761), sulfenylthiocarbonates (Brois et al., *J. Am. Chem. Soc.*, 1970, 92, 7629), sulfenyl hydrazines (Mukaiayama et al., *Tetrahedron Lett.*, 1968, 5907), 2,2'-dithiopyridyl disulfide and others (Matsueda et al., *Chem. Lett.*, 1981, 737; Barton et al., *J. Org. Chem.*, 1991, 56, 6697) and 2,2'-dithiobenzothiazole disulfide (E. Brzezinska and Ternay, *J. Org. Chem.*, 1994, 59, 8239).

Mixed disulfides can also be obtained by reaction of a thiol with sulfenyl halides (Küele, *Synthesis*, 1970, 561; Küele, *Synthesis*, 1971, 563).

However, the use of these various methods in synthesis and in particular in the nucleoside series encounters a major disadvantage, which is the use of a thiol functional group which is unstable because of its ready oxidation in the air, which results in the symmetrical disulfide. This functional group is also highly reactive and can present a problem in the case of multifunctional compounds. In the nucleoside series, the introduction of a thiol functional group requires recourse to methods for protecting and deprotecting the alcohol and amine functional groups. Moreover, the instability of the functional group carried, for example, in the 2' position of nucleosides has been demonstrated (Johnson et al., *Tetrahedron*, 1995, 51, 5093).

After the studies of the Fuchs group (Anderson et al., *J. Org. Chem.*, 1988, 53, 3125), Chambert et al. (*J. Org. Chem.*, 2000, 65, 249) proposed a method for the synthesis of methyl disulfides, of formula R—S—S—$CH_3$ where R represents a nucleoside, which avoids passing through unstable nucleoside thiols. This method consists in preparing a very stable sulfide intermediate compound, a 2-(trimethylsilyl)ethyl sulfide, of formula R—S—$CH_2$—$CH_2$—Si $(CH_3)_3$. Such intermediates can formed by reaction of 2-(trimethylsilyl) ethanethiol, which can be easily prepared in the laboratory in a large amount (Stamm, *J. Org. Chem.*, 1963, 3264), or by radical reaction of trimethylvinylsilane with a thiol (Mahadevan et al., Synth. Commun., 1994, 3099). The intermediate 2-(trimethylsilyl)ethyl sulfide, obtained in the nucleoside series according to the first method mentioned, is subsequently reacted with dimethyl(methylthio)sulfonium tetrafluoroborate in order to obtain the corresponding methyl disulfides. The authors thus prepared the 2'-methyl disulfides of 2'-deoxyuridine, 2'-deoxycytidine and 3'-deoxythymidine respectively.

More recently, in the paper by S. Chambert et al. (*J. Org. Chem.*, 2002, 67, 1898-1904), the same authors demonstrated the advantage of the abovementioned intermediate 2-(trimethylsilyl)ethyl sulfides in the preparation of thiocyanates, in particular nucleoside thiocyanates, by reaction in methanol with cyanogen bromide. During these studies, the authors also discovered that this same reaction, when it is carried out in dichloromethane, results in the corresponding symmetrical disulfide of formula R—S—S—R when R represents 2'-deoxyuridine substituted in 2' position.

It emerges from these studies that 2-(trimethylsilyl)ethyl sulfides, of formula R—S—$CH_2$—$CH_2$—Si $(CH_3)_3$, constitute determining intermediates in the synthesis of methyl disulfides. The synthetic route used by Chambert et al. makes it possible to selectively access mixed methyl nucleoside disulfides without having recourse to protecting the alcohol and amine functional groups of the nucleosides. However, in the context of a "prodrug" approach, it is advantageous to be able to synthesize a disulfide combining a first active nucleoside component and a second component carrying a second vector thiol functional group and/or bioactive component. Access to novel mixed disulfides makes it possible to enrich the range of potentially active molecules.

The authors of the present invention have discovered that the above 2-(trimethylsilyl)ethyl sulfides can constitute the starting point for the synthesis of a large number of mixed or symmetrical disulfides but also the starting point for the synthesis of thiosulfinate compounds.

The latter can be obtained by oxidation of mixed or symmetrical disulfides (Colonna et al., *Eur. J. Org. Chem.*, 2005, 1727; Liu et al., *J. Am. Chem. Soc.*, 1997, 117, 9913) or by [2,3]-sigmatropic rearrangement when the disulfides are of dialkoxy allyl or propargyl type (Bravermen et al., *Tetrahedron Lett.*, 2004, 45, 8235). Likewise, the reaction between benzenesulfinyl azide and various thiols results in the preparation of thiosulfinates (Maricich et al., *J. Org. Chem.*, 1984, 49, 1931), and also the reaction of the alkenesulfenate anion with trimethylsilyl halides (Refyik et al., *Can. J. Chem.*, 1998, 76, 213).

Thiosulfinates can result in disulfides, sulfinic acids, sulfoxides and thiosulfonates (Lacombe, *Reviews Heteroatom. Chem.*, 1999, 21, 1). They exist in the form of two enantiomers or of two diasteroisomers when the functional group is carried by the sugar in the nucleoside series. These are thus also advantageous intermediates in asymmetric synthesis (see, for example, Liu et al., J. Org. Chem., 1997, 119, 9913). Moreover, some of them are natural products having advantageous biological properties; for example, they exhibit antimicrobial and/or anti-inflammatory activities (Whitmore et al., *Nat. Food Antimicrob. Syst.*, 2000, 349).

A subject matter of the present invention is a process for the preparation of a compound corresponding to the general formula (I) R1-S(O)$_x$—S(O)$_y$—R2,
in which R1 represents a hydrocarbon molecular residue which can be substituted and/or interrupted by one or more atoms and/or by one or more groups comprising one or more atoms, said atoms being chosen from N, O, P, S, Si or X, where X represents a halogen; R2 represents, independently of R1, a carbon group or a hydrocarbon molecular residue which can be substituted and/or interrupted by one or more atoms and/or by one or more groups comprising one or more atoms, said atoms being chosen from N, O, P, S, Si or X, where X represents a halogen, and x and y are chosen from 0 and 1 such that the sum of x and y is at most equal to 1.

The authors have developed reaction conditions which form the subject matter of the present invention and which make it possible to obtain, starting from an intermediate compound of general formula (II) R1-S(O)$_x$—R3-Si(R4)(R5)(R6) (IIa for x=0 and IIb for x=1) in which R3 represents a saturated and/or unsaturated and/or substituted hydrocarbon chain of two carbon atoms, compounds of general formula (I) which encompass in particular all the groups of compounds which follow:

(III) R1-S—S—R2, mixed disulfide compounds of formula I where x=y=0,
(IV) R1-S—SO—R2, thiosulfinate compounds of formula I where x=0 and y=1,
(V) R1-SO—S—R2, thiosulfinate compounds of formula I where x=1 and y=0,
(VI) R1-S—S—R1, symmetrical disulfide compounds, in which formulae (III), (IV), (V) and (VI) R1 and R2 have the definition given above.

Thus, a subject matter of the present invention is a process for the preparation of compounds of formula (I) R1-S(O)$_x$—S(O)$_y$—R2 as defined above, according to which a compound of formula (II) R1-S(O)$_x$—R3-Si(R4)(R5)(R6), in which R3 represents a saturated and/or unsaturated and/or substituted hydrocarbon chain of two carbon atoms and R4, R5 and R6, which are identical or different, each represent, independently of one another, a hydrocarbon group, is reached with a compound of formula (VII) R2-S(O)$_y$—X, where X represents a halogen and R2 and y have the definitions given above (VIIa when y=0 and VIIb when y=1).

According to this process, it is thus possible, according to the invention, to obtain a disulfide of formula (III) R1-S—S—R2 by reacting a compound of formula (IIa) R1-S—R3-Si(R4)(R5)(R6) with a compound of formula (VIIa) R2-S—X, R1 and R2 being identical in order to form symmetrical disulfides or different in order to form mixed disulfides.

According to this process, it is also possible, according to the invention, to obtain a thiosulfinate of formula (IV) R1-S—SO—R2 by reacting a compound of formula (IIa) R1-S—R3-Si(R4)(R5)(R6) with a sulfinyl halide of formula (VIIb) R2-SO—X.

The process of the invention also makes it possible to obtain a thiosulfinate of formula (V) R1-SO—S—R2, as follows:
the compound of formula (IIa) R1-S—R3-Si(R4)(R5)(R6) is oxidized in order to obtain a compound of formula (IIb) R1-SO—R3-Si(R4)(R5)(R6), then
the compound of formula (IIb) is reacted with a sulfenyl halide of formula (VIIa) R2-S—X.

The reactions involved in the processes of the invention and the various compounds of formula (I) capable of being obtained are illustrated below starting from the compound (IIa) where R3 represents —CH$_2$—CH$_2$ and R4, R5 and R6 each represent —CH$_3$, without, however, the scope of the invention being limited to these R3, R4, R5 and R6 groups.

According to the invention, in order to obtain a mixed disulfide of formula (III) above, a compound of formula (IIa) R1-S—R3-Si(R4)(R5)(R6) is reacted with a compound of formula (VIIa) R2-S—X

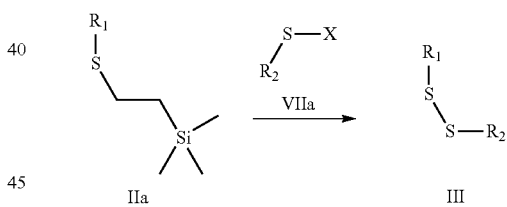

In order to prepare a thiosulfinate of formula (IV) according to the invention, the compound of formula (IIa) R1-S—R3-Si(R4)(R5)(R6) is reacted with a compound of formula (VIIb) R2-SO—X. The reaction involved is represented below starting from the compound (IIa) where R3 represents ethyl and R4, R5 and R6 each represent methyl:

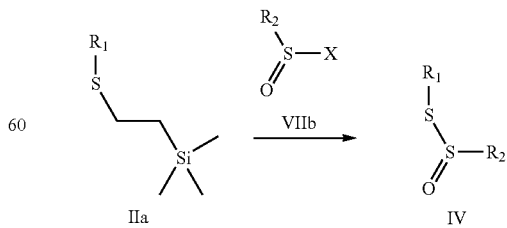

A thiosulfinate of formula (V) is also obtained by reacting a compound of formula (IIb) R1-SO—R3-Si(R4)(R5)(R6)

with a compound of formula (VIIa) R2-S—X, the compound (IIb) being obtained by oxidizing the compound of formula (IIa).

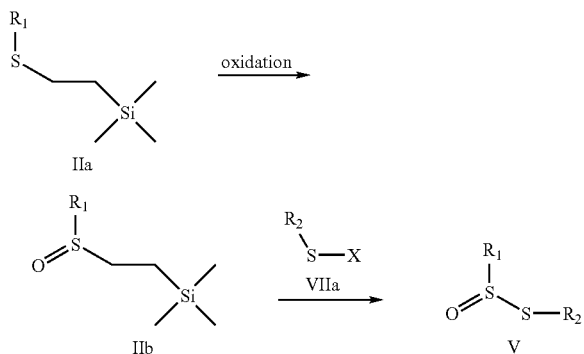

Advantageously, the reaction of the compound (IIa) with a compound (VIIa) or (VIIb), in order to prepare a mixed disulfide (III) and in order to prepare a thiosulfinate (IV) respectively, and the reaction of the compound (IIb) with a compound (VIIa), in order to obtain a thiosulfinate (V), can be carried out in the presence of fluoride ions, in a preferably catalytic amount. The fluoride ions are preferably contributed by an ammonium fluoride, a tetrabutylammonium fluoride, a triethylammonium fluoride or their mixtures.

Starting from the same intermediate of formula (IIa), the authors have discovered that, in the preparation of mixed disulfides of formula (III), the compound (VIIa) R2-S—X can be formed in situ, in the reaction medium comprising the intermediate (IIa) and a compound of formula (VIII) R2-S—S—R2, in the presence of $X_2$ or XCN, where X represents a halogen. The intermediate (IIa) then reacts with the compound (VIIa) thus formed, to result in the mixed disulfide (III). This reaction of the compound (IIa) with the compound (VIIa) formed in situ can advantageously be carried out in the presence of fluoride ions. The latter can be contributed by an ammonium fluoride, a tetrabutylammonium fluoride, a triethylammonium fluoride or their mixtures and they are preferably present in a catalytic amount.

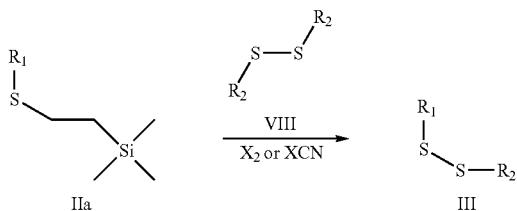

Likewise, the preparation of symmetrical disulfides of formula (VI) can be carried out starting from the compound (IIa), in the presence of a dihalide $X_2$ or a cyanogen halide. This reaction can advantageously be carried out in the presence of fluoride ions. The latter can be contributed by an ammonium fluoride, a tetrabutylammonium fluoride, a triethylammonium fluoride or their mixtures and they are preferably present in a catalytic amount.

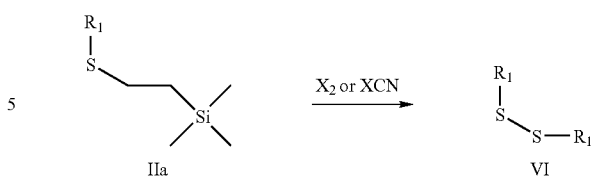

The invention also relates to a process for the preparation of a compound corresponding to the formula (III'),

R1-S—S—R2' in which R1 represents a hydrocarbon molecular residue which can be substituted and/or interrupted by one or more atoms and/or by one or more groups comprising one or more atoms, said atoms being chosen from N, O, P, S, Si or X, where X represents a halogen; R2' represents, independently of R1, a carbon group or a hydrocarbon molecular residue which may be substituted and/or interrupted by one or more atoms and/or by one or more groups comprising one or more atoms, said atoms being chosen from N, O, P, S, Si or X, where X represents a halogen, comprising the following stages:
a compound (III) is obtained according to the process of the invention defined above, then the compound (III) is reacted with a compound of formula R2'-SH.

Before describing in more detail and illustrating the various subject matters of the invention, the R1-R6 groups of the compounds involved in the processes of the invention and of the compounds obtained according to the invention are defined more precisely below. Without departing from the scope of the invention, the following definitions are to be regarded independently of one another or in combination with one another.

The term "molecular residue" is understood to mean the residue of a biological molecule which is optionally modified, chemically or otherwise. Thus, R1 advantageously represents, according to the invention, a nucleoside molecular residue chosen from nucleosides and modified nucleosides. The term "modified nucleosides" is understood to mean any modification made to the sugar and/or the base, in particular by one or more substitutions, one or more unsaturations, or an isomerism, for example structural isomerism. Thus, R1 can represent a molecular residue chosen from 2'-deoxyribonucleosides, 3'-deoxyribonucleosides, 2',3'-dideoxyribonucleosides, 2',3'-dideoxy-2',3'-di-dehydroribonucleosides and their derivatives; by way of examples, R1 represents a molecular residue chosen from 2'-deoxyuridine, 2',3'-dideoxyuridine, 2',3'-dideoxy-2',3'-didehydrouridine, 2'-deoxycytidine, 2',3'-dideoxycytidine, 2',3'-dideoxy-2',3'-didehydrocytidine, 3'-deoxythymidine, 3'-deoxy-2',3'-dehydrothymidine and their derivatives; advantageously, when R1 represents a molecular residue chosen from 2'-deoxyribonucleosides, 3'-deoxyribonucleosides and 2',3'-dideoxy-ribonucleosides, then the S atom is bonded to the carbon in the 2' position or to the carbon in the 3' position of the ribose of the nucleoside and, when R1 represents a molecular residue chosen from 2',3'-dideoxy-2',3'-dehydroribonucleosides, then the S atom is bonded to the carbon in the 2' position or to the carbon in the 3' position of the ribose; R1 can also represent an amino acid residue which is optionally modified.

R2 and R2' advantageously represent a halocarbon group or a linear or branched, or aromatic, hydrocarbon molecular residue comprising atoms chosen from N and O. According to preferred alternative forms, R2 represents a carbon group chosen from alkyl, aryl or alkylaryl groups which is optionally substituted and/or interrupted by one or more atoms and/or by one or more groups comprising one or more atoms, said atoms being chosen from N, O, S, P, S, Si and X, where X represents a halogen; R2 is then preferably chosen from ortho-nitrophenyl, para-nitrophenyl and trichloromethyl groups when the fluoride ions are not used. According to other alternative forms, R2 represents a molecular residue, in particular as defined above. It can be chosen from ribonucleosides, 2'-deoxyribonucleosides, 2',3'-dideoxyribonucleosides and 2',3'-dideoxy-2',3'-dehydroribonucleosides.

R3 advantageously represents an alkyl group of 1 to 6 carbon atoms and better still the —CH$_2$—CH$_2$ group.

R4, R5 and R6, which are identical or different, advantageously represent an alkyl group comprising from 1 to 6 carbon atoms, representative components of which are, for example, as follows: the methyl, ethyl, n-propyl, isopropyl, n-butyl, sec-butyl, isobutyl, tert-butyl, pentyl or hexyl groups. Preferably, R4, R5 and R6 are identical and represent a methyl group.

Another subject matter of the invention is a process for the preparation of a thiol chosen from thiols corresponding to the following formulae R1-SH, R2-SH and R2'-SH, in which formula R1 represents a hydrocarbon molecular residue which can be substituted and/or interrupted by one or more atoms and/or by one or more groups comprising one or more atoms, said atoms being chosen from N, O, P, S, Si or X, where X represents a halogen; R2 or R2' represents a carbon group or a hydrocarbon molecular residue which can be substituted and/or interrupted by one or more atoms and/or by one or more groups comprising one or more atoms, said atoms being chosen from N, O, P, S, Si or X, where X represents a halogen, said process being characterized in that the preparation is carried out of a disulfide according to the invention, that is to say of a disulfide of formula (III), in order to obtain the thiol R1-SH, or of a disulfide of formula (VI), in order to obtain the thiol R2-SH, or of a disulfide of formula (III'), in order to obtain the thiol R2'-SH, the definitions of R1, R2 and R2' and the reaction conditions being chosen from those defined above in the context of the invention, and the disulfide thus obtained is reduced.

Another subject matter of the invention is a process for the synthesis of disulfide compounds of formula (III) R1-S—S—R2 where R1 represents an amino acid residue. This process can result in sulfur-comprising amino acids 61, according to the synthetic scheme below which is illustrated in the experimental part of the description.

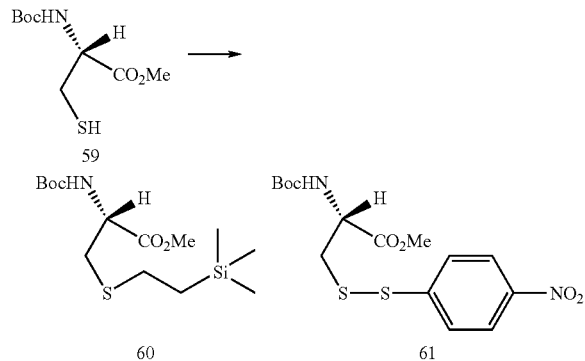

The invention also relates to novel compounds obtained according to the invention. The preparation of the compounds carrying a reference is illustrated later in the description.

Thus, it relates to compounds of formula (IIa)

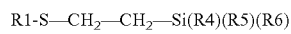

as intermediate compounds in the preparation of disulfides and thiosulfinates, chosen from:
2',3'-dideoxy-3'-(2-(trimethylsilyl)ethyl)thiouridine 35
5-bromo-2',3'-dideoxy-3'-(2-(trimethylsilyl)ethyl)thiouridine 36-1
2'-deoxy-2'-(2-(trimethylsilyl)ethyl)thiothymidine 46
2'-deoxy-3'-(O-mesyl)-2'-(2-(trimethylsilyl)ethyl)thiouridine 47
5'-O-(tert-butyldiphenylsilyl)-2'-(2-(tri-methylsilyl)ethyl)thiocytidine 48
N-4-benzoyl-3'-(O-mesyl)-5'-(O-tert-butyldiphenylsilyl)-2'-(2-(trimethylsilyl)ethyl)thio-cytidine 49
1-(3'-(2-(trimethylsilyl)ethylthio)-β-D-xylofuranos-1'-yl) thymine 52
2,2'-anhydro-5'-(O-benzoyl)-1-(3'-(2-(trimethylsilyl)ethylthio)-β-D-xylofuranos-1'-yl)thymine 53
2',3'-dideoxy-3'-(2-(trimethylsilyl)ethyl)thiocytidine 55

The invention in addition relates to compounds of formula (IIa)

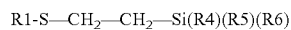

as intermediate compounds in the preparation of disulfides and thiosulfinates, in which formula (IIa) R1 is chosen from 2',3'-didehydro-2',3'-dideoxynucleoside groups and R4, R5 and R6, which are identical or different, each represent, independently of one another, an alkyl or aryl group. Preferred compounds are chosen from the following:
2',3'-Didehydro-2',3'-dideoxy-2'-(2-(trimethyl-silyl)ethyl) thiothymidine 14
2',3'-Didehydro-2',3'-dideoxy-3'-(2-(trimethyl-silyl)ethyl) thiothymidine 54
2',3'-Didehydro-2',3'-dideoxy-2'-(2-(trimethyl-silyl)ethyl) thiouridine 18
2',3'-Didehydro-2',3'-dideoxy-5'-(O-tert-butyl-diphenylsilyl)-2'-(2-(trimethylsilyl)ethyl)thiocytidine 50
2',3'-Didehydro-2',3'-dideoxy-2'-(2-(trimethyl-silyl)ethyl) thiocytidine 19

Other subject matters of the invention are as follows: Compounds of formula (IIb) R1-SO—R3-Si(R4)(R5)(R6), as intermediate compound in the preparation of thiosulfinates of formula (V), chosen from:
3'-deoxy-3'-(2-(trimethylsilyl)ethyl)thiothymidine sulfoxide 28
2'-deoxy-2'-(2-(trimethylsilyl)ethyl)thiouridine sulfoxide 32

Compounds of formula (III) R1-S—S—R2, in which R1 represents a 2'- or 3'-deoxynucleoside or a 2',3'-dideoxy-2',3'-didehydronucleoside; such compounds are illustrated by the following compounds:
3'-Deoxythymidin-3'-yl trichloromethyl disulfide 2
3'-Deoxythymidin-3'-yl 4-nitrophenyl disulfide 3
2'-Deoxyuridin-2'-yl trichloromethyl disulfide 7
2'-Deoxycytidin-2'-yl trichloromethyl disulfide 8
2'-Deoxyuridin-2'-yl 4-nitrophenyl disulfide 9
2'-Deoxycytidin-2'-yl 4-nitrophenyl disulfide 10
2'-Deoxyuridin-2'-yl 2-nitrophenyl disulfide 11
2'-Deoxycytidin-2'-yl 2-nitrophenyl disulfide 12
3'-Deoxythymidin-3'-yl propyl disulfide 13
2',3'-Didehydro-2',3'-dideoxythymidin-2'-yl trichloromethyl disulfide 15
2',3'-Didehydro-2',3'-dideoxythymidin-2'-yl 4-nitro-phenyl disulfide 16
2',3'-Didehydro-2',3'-dideoxythymidin-2'-yl 2-nitro-phenyl disulfide 17

2',3'-Didehydro-2',3'-dideoxyuridin-2'-yl trichloromethyl disulfide 20

2',3'-Didehydro-2',3'-dideoxyuridin-2'-yl 4-nitrophenyl disulfide 21

2',3'-Didehydro-2',3'-dideoxyuridin-2'-yl 2-nitrophenyl disulfide 22

2',3'-Dideoxyuridin-3'-yl methyl disulfide 56

2'3'-Dideoxycytidin-3'-yl methyl disulfide 57

5-Bromo-2',3'-dideoxyuridin-3'-yl methyl disulfide 58

Compounds of formula (IV) R1-S—SO—R2 are illustrated by the thiosulfinates 25 and 27.

Compounds of formula (V) R1-SO—S—R2 are chosen from the thiosulfinates 29, 30 and 33.

Compounds of formula (III') R1-S—S—R2' are chosen from:

Allyl 3'-deoxythymidin-3'-yl disulfide 37

3'-Deoxythymidin-3'-yl 2-hydroxyethyl disulfide 38

2-Aminoethyl 3'-deoxythymidin-3'-yl disulfide hydrochloride 39

Butyl 3'-deoxythymidin-3-yl disulfide 40

3-Deoxythymidin-3'-yl hexyl disulfide 41

3'-Deoxythymidin-3'-yl octyl disulfide 42

3'-Deoxythymidin-3'-yl 6-hydroxyhexyl disulfide 43

Compounds of formula (VI) R1-S—S—R1 are chosen from the following disulfides:

Bis(5-bromo-2',3'-dideoxyuridin-3'-yl) disulfide 36

Bis(2',3'-didehydro-2',3'-dideoxyuridin-2'-yl) disulfide 45

The references allocated to the compounds are given again in the experimental part below, in which the preparation of these compounds according to the invention is illustrated.

The subject matters of the invention are now illustrated by the following examples. These relate more particularly to the preparation of nucleoside disulfide or thiosulfinate compounds but do not in any way constitute a limitation of the invention to the preparation of these compounds.

EXAMPLE 1

Preparation of a Mixed Disulfide of Formula (III) from an Intermediate (IIa) and a Sulfenyl Halide (VIIa)

Preparation of Mixed 3'-deoxythymidine 3'-disulfides 1 from a Stable Sulfenyl Halide

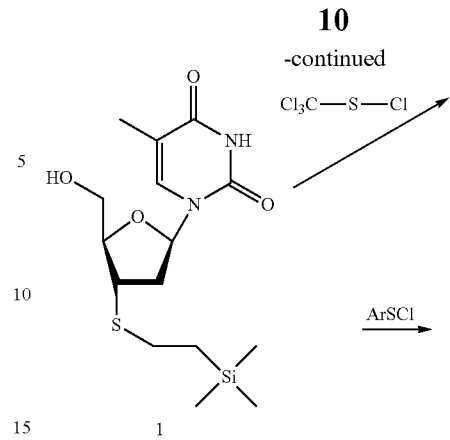

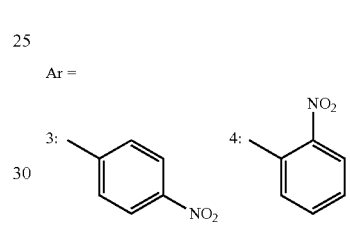

Preparation of Mixed 2'-deoxyuridine 2'-disulfides 7, 9 and 11 and of mixed 2"-deoxycytidine 2'-disulfides 8, 10 and 12 from a Stable Sulfenyl Halide

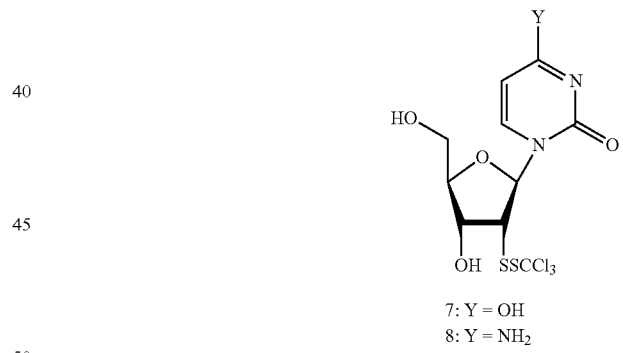

7: Y = OH
8: Y = NH$_2$

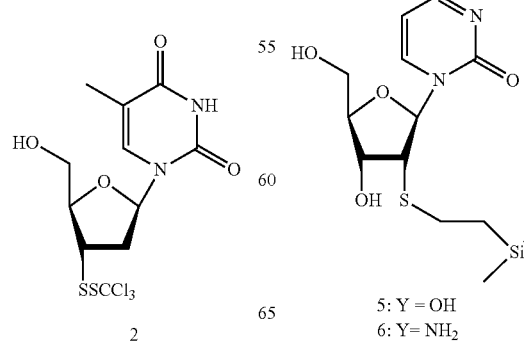

5: Y = OH
6: Y = NH$_2$

-continued

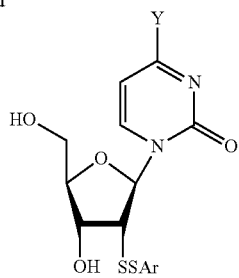

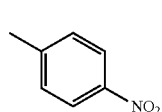
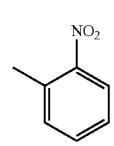

Ar =

9: Y = OH
10: Y = NH$_2$

11: Y = OH
12: Y = NH$_2$

This process can be used for the preparation of sulfur-comprising amino acids. This alternative form is illustrated in the experimental part of the description with the preparation of the compounds 60 and 61.

EXAMPLE 2

Preparation of a Mixed Disulfide of Formula (III) from an Intermediate (IIa) and from a Sulfenyl Halide (VIIa) Formed in situ Preparation of a Mixed 3"-deoxythymidine 3'-disulfide 13 from a Sulfenyl Halide (VIIa) Formed in situ from a Propyl Disulfide (VIII) in the Presence of Bromine (Br$_2$) or of Cyanogen Bromide

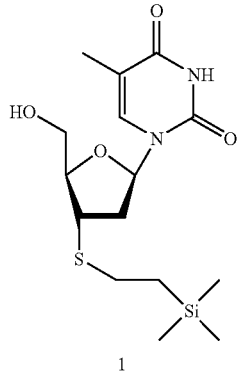

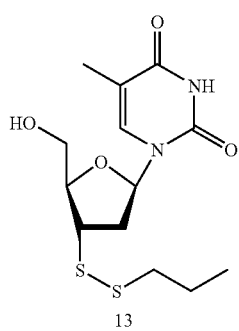

EXAMPLE 3

Preparation of Mixed Disulfides of Vinyl Disulfide Type of Formula (III) from an Intermediate (IIa) and from a Sulfenyl Halide (VIIa)

Preparation of Mixed 2',3'-dideoxy-2',3'-didehydroribo-nucleoside (Thymidine, Uridine and Cytidine) 2'-disulfides 15 to 17 and 20 to 22 from a Stable Sulfenyl Halide

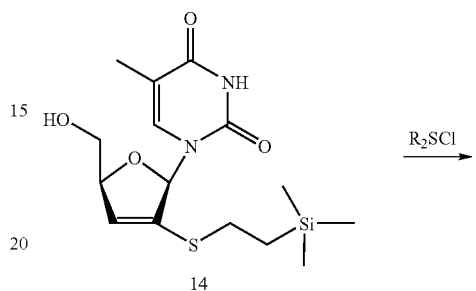

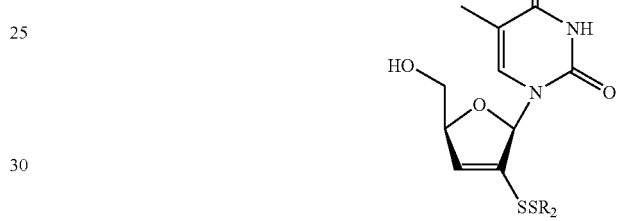

15: R$_2$ = —CCl$_3$
16: R$_2$ = -Ph4-NO$_2$
17: R$_2$ = -Ph2-NO$_2$

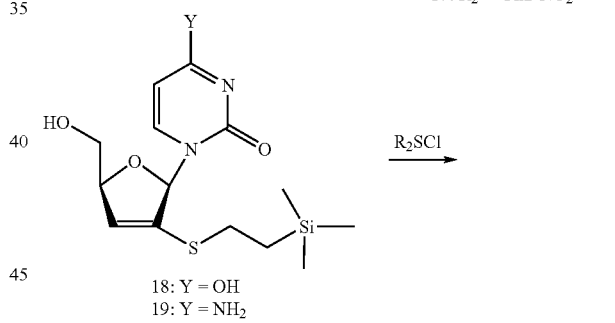

18: Y = OH
19: Y = NH$_2$

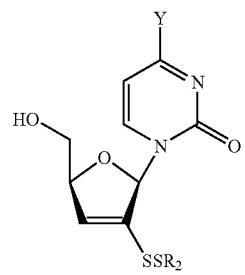

20: Y = OH, R$_2$ = —CCl$_3$
21: Y = OH, R$_2$ = -Ph4-NO$_2$
22: Y = OH, R$_2$ = -Ph2-NO$_2$

The protocols for the synthesis of the disulfides 15, 16, 17, 20, 21 and 22 are described in more detail in the continuation of the description.

These reactions can be repeated with nucleosides comprising other nucleic bases, such as cytosine, and other nucleoside or nonnucleoside unsaturated silylated sulfides.

According to the reaction scheme indicated below, the vinyl disulfide thus formed can be reduced in situ to form the corresponding vinyl thiol. The latter, which is highly unstable, is alkylated in situ. This process constitutes a simple and mild method for obtaining a thiol.

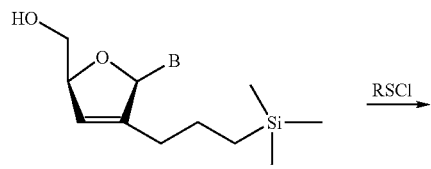

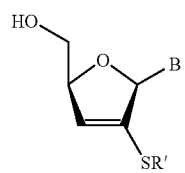

EXAMPLE 4

Preparation of Thiosulfinates of Formula (IV) from an Intermediate (IIa) and a Sulfinyl Halide (VIIb)

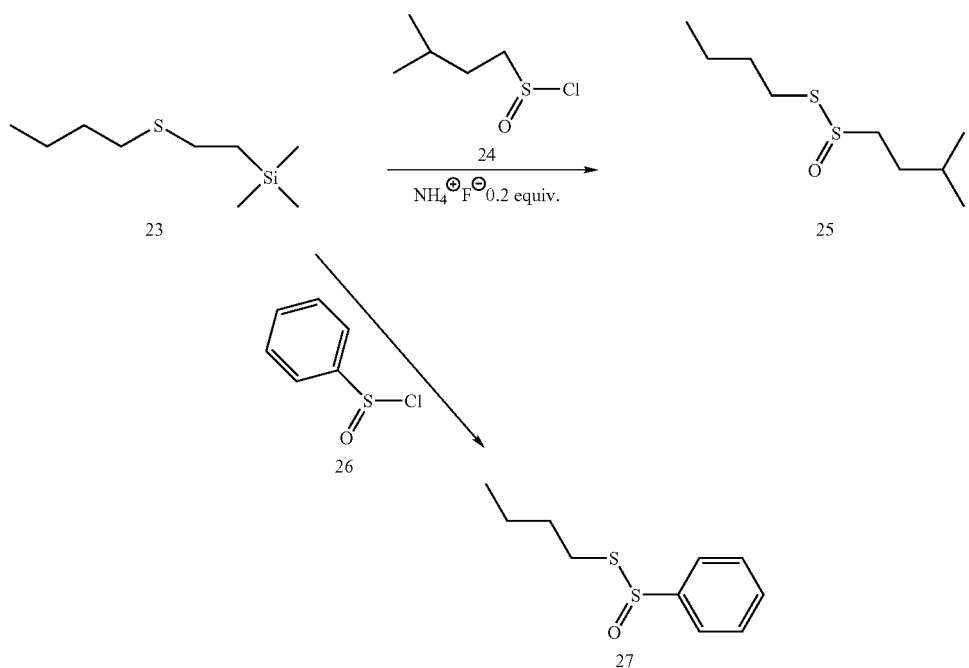

-continued

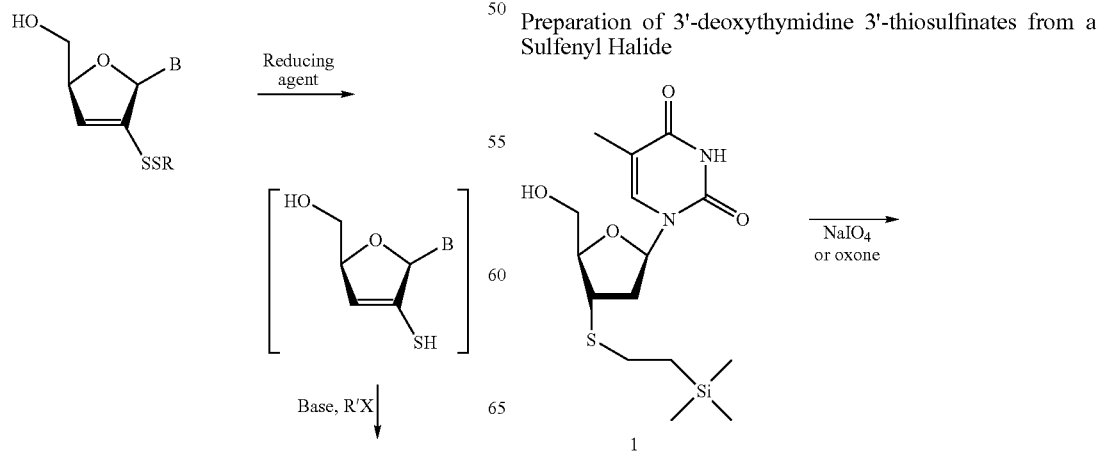

EXAMPLE 5

Preparation of a Thiosulfinate of Formula (V) from an Intermediate (IIb) and a Sulfenyl Halide (VIIa)

Preparation of 3'-deoxythymidine 3'-thiosulfinates from a Sulfenyl Halide

-continued

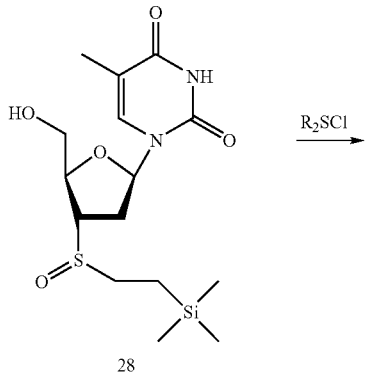

28

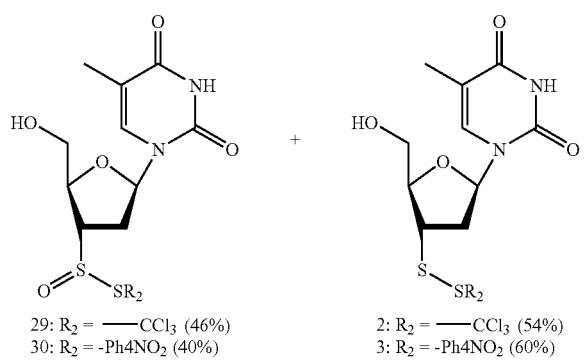

29: R₂ = —CCl₃ (46%)
30: R₂ = -Ph4NO₂ (40%)

2: R₂ = —CCl₃ (54%)
3: R₂ = -Ph4NO₂ (60%)

This example can be repeated for the preparation of thiosulfinates of other nucleosides (2'-deoxycytidine, uridine, cytidine, and the like).

EXAMPLE 6

Enantioselective Preparation of Nucleoside Thiosulfinates of Formula (V) by Reaction of an Intermediate (IIb) with a Sulfenyl Halide (VIIa)

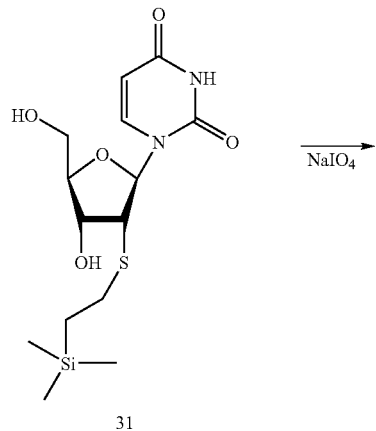

31

-continued

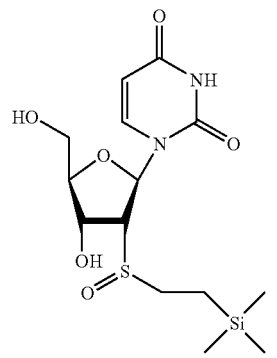

32a: S isolated with a yield of 38.5%
32b: R isolated with a yield of 31.5%

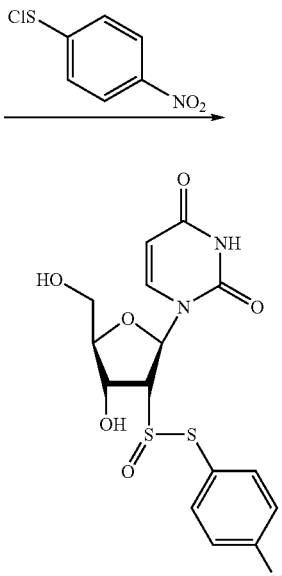

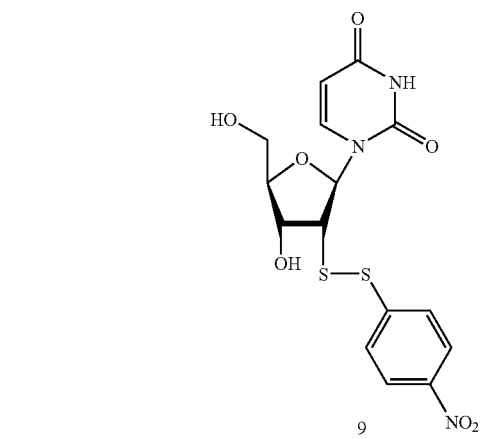

33: essentially just one
of the 2 possible
diastereoisomers (NMR)

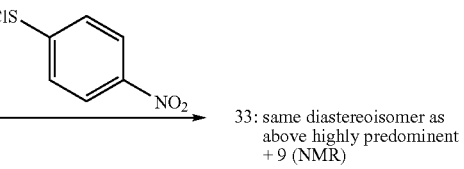

9

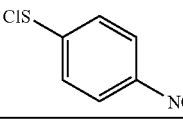

32b: R

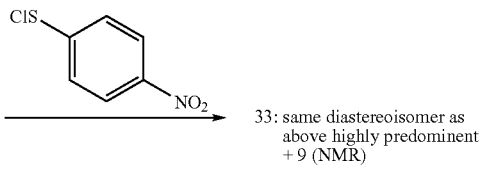

33: same diastereoisomer as
above highly predominent
+ 9 (NMR)

EXAMPLE 7

Preparation of Symmetrical Disulfides (Vi) from an Intermediate (IIa) in the Presence of Cyanogen Bromide or Dibromine

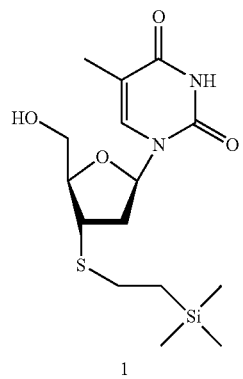
1

BrCN or Br₂ →

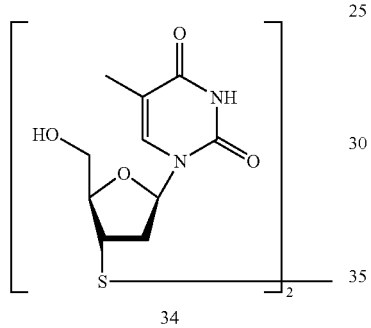
34

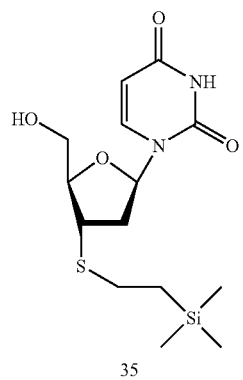
35

BrCN →

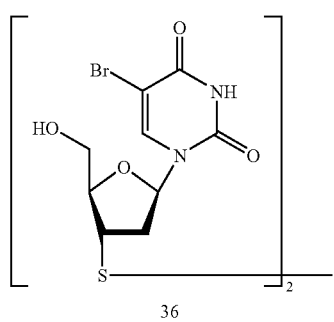
36

EXAMPLE 8

Preparation of Other Disulfides (III) from the Intermediate (IIa)

The nucleoside 4-nitrophenyl disulfide 3 prepared was used to prepare novel mixed nucleoside alkyl disulfides:

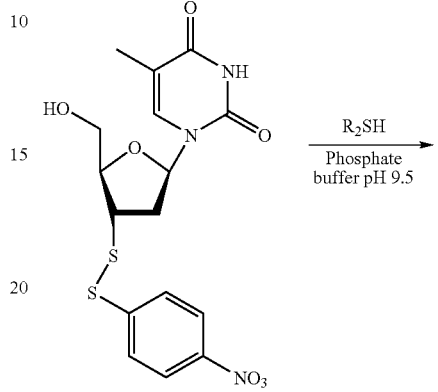
3

$R_2SH$ / Phosphate buffer pH 9.5 →

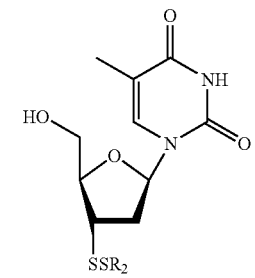

37: $R_2 =$ —$CH_2$—CH=$CH_2$
38: $R_2 =$ —$CH_2$—$CH_2$—OH
39: $R_2 =$ —$CH_2$—$CH_2$—$NH_2$
40: $R_2 = $-$nC_4H_9$
41: $R_2 = $-$nC_6H_{13}$
42: $R_2 = $-$nC_8H_{17}$
43: $R_2 = $-$nC_6H_{12}$—OH

EXAMPLE 9

Preparation of Novel Vinyl Thiols from a Vinyl Disulfide Intermediate (III)

21

Reducing agent →

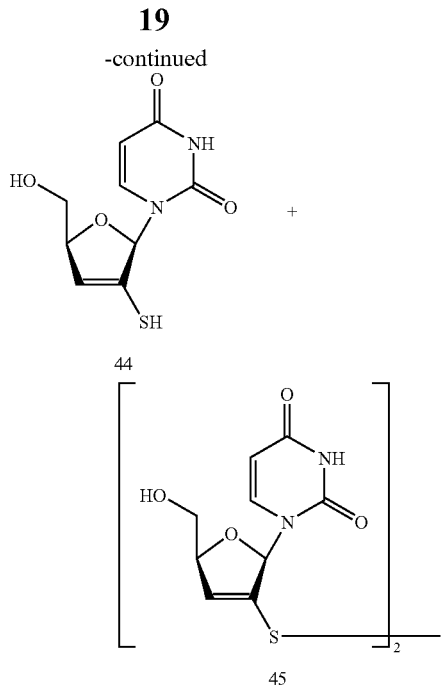

This reaction can be carried out with the nucleosides 15 to 17 and 20 to 22 and all the derivatives (III).

The experimental part below describes the synthetic protocols followed in order to obtain mixed disulfides obtained according to the invention by the process which forms the subject matter of example 1.

Protocol A1: Synthesis of Nucleoside/4-Nitrophenyl Disulfide Derivatives

4-Nitrobenzenesulfenyl chloride (3 equivalents) is added to a solution, maintained under argon, of nucleoside in anhydrous dichloromethane. The mixture is left stirring for 15 hours and then the solvent is evaporated. The residue obtained is taken up in the minimum amount of dichloromethane in order to be chromatographed on silica gel in a dichloromethane-methanol (98:2 then 95:5) mixture to give the expected compound.

Protocol A2: Synthesis of Nucleoside/4-Nitrophenyl Disulfide Derivatives

4-Nitrobenzenesulfenyl chloride (3 equivalents) is added to a solution, maintained under argon, of nucleoside in anhydrous methanol. The mixture is left stirring for 15 hours then the solvent is evaporated. The residue obtained is taken up in the minimum amount of dichloromethane in order to be chromatographed on silica gel in a dichloromethane-methanol (95:5 then 90:10) mixture to give the expected compound.

Protocol B1: Synthesis of Nucleoside/2-nitrophenyl Disulfide Derivatives

2-Nitrobenzenesulfenyl chloride (3 equivalents) is added to a solution, maintained under argon, of nucleoside in anhydrous dichloromethane. The mixture is left stirring for 15 hours and then the solvent is evaporated. The residue obtained is taken up in the minimum amount of dichloromethane in order to be chromatographed on silica gel in a dichloromethane-methanol (98:2 then 95:5) mixture to give the expected compound.

Protocol B2: Synthesis of Nucleoside/2-nitrophenyl Disulfide Derivatives

2-Nitrobenzenesulfenyl chloride (3 equivalents) is added to a solution, maintained under argon, of nucleoside in anhydrous methanol. The mixture is left stirring for 15 hours then the solvent is evaporated. The residue obtained is taken up in the minimum amount of dichloromethane in order to be chromatographed on silica gel in a dichloromethane-methanol (95:5 then 90:10) mixture to give the expected compound.

Protocol B3: Synthesis of Nucleoside/2-nitrophenyl Disulfide Derivatives

2-Nitrobenzenesulfenyl chloride (3 equivalents) is added to a solution, maintained under argon, of nucleoside in anhydrous dichloroethane. The mixture is left stirring and is brought to reflux for 48 hours. The solvent is evaporated and the residue obtained is taken up in the minimum amount of dichloromethane in order to be chromatographed on silica gel in a dichloromethane-methanol (98:2 then 95:5) mixture to give the expected compound.

Protocol C1: Synthesis of Nucleoside/Trichloromethane Disulfide Derivatives

Trichloromethanesulfenyl chloride (3 equivalents) is added to a solution, maintained under argon, of nucleoside in anhydrous dichloromethane. The mixture is left stirring overnight and then the solvent is evaporated under a stream of nitrogen in a hood due to the toxicity of the reactant used. The residue obtained is taken up in the minimum amount of eluent in order to be chromatographed on silica gel in a dichloromethane-methanol (95:5) mixture and to give the expected compound.

Protocol C2: Synthesis of Nucleoside/Trichloromethane Disulfide Derivatives

Trichloromethanesulfenyl chloride (3 equivalents) is added to a solution, maintained under argon, of nucleoside in anhydrous methanol. The mixture is left stirring overnight and then the solvent is evaporated under a stream of nitrogen in a hood due to the toxicity of the reactant used. The residue obtained is taken up in the minimum amount of eluent in order to be chromatographed on silica gel in a dichloromethane-methanol (95:5) mixture and to give the expected compound.

Protocol C3: Synthesis of Nucleoside/Trichloromethane Disulfide Derivatives

Trichloromethanesulfenyl chloride (3 equivalents) is added to a solution, maintained under argon, of nucleoside in anhydrous dichloromethane. The mixture is left stirring and is brought to reflux for 48 hours. The solvent is subsequently evaporated under a stream of nitrogen in a hood due to the toxicity of the reactant used. The residue obtained is taken up in the minimum amount of eluent in order to be chromatographed on silica gel in a dichloromethane-methanol (95:5) mixture and to give the expected compound.

3'-Deoxythymidin-3'-yl trichloromethyl disulfide 2

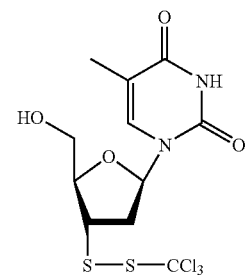

Protocol C1

3'-Deoxy-3'-(2-(trimethysilyl)ethyl)thiothymidine 1 (40 mg; 0.11 mmol)

Anhydrous dichloromethane (1.5 ml)

Trichloromethanesulfenyl chloride (60 µl, 0.56 mmol) 2 (37 mg, 0.09 mmol, 81%) in the form of a white powder.

$^1$H NMR (400 MHz, CDCl$_3$) δ 9.36 (1 H, s, NH), 7.48 (1 H, s, 6-H); 6.13 (1 H, dd, J=6.4 Hz, J=12.7 Hz, 1'-H), 4.26 (1 H, m, 3'-H), 4.18 (1 H, m, 4'-H), 4.09-3.88 (2 H, m, 5'-H×2), 2.77-2.56 (2 H, m, 2'-H×2).

$^{13}$C NMR (100 MHz, CDCl$_3$) δ 163.9 (C2), 150.4 (C4), 136.7 (C6), 115.2 (C5), 100.4 (C—Cl$_3$), 86.2 (C1'), 85.4 (C4'), 61.3 (5'-CH$_2$), 47.9 (C3'), 38.4 (2'-CH$_2$), 12.5 (5-CH$_3$).
MS (DCI, NH$_3$-isobutane): m/z 409 [M+H]$^+$, 429 [M+NH$_3$]$^+$, 127 [thymine+H]$^+$.
High resolution MS:
type of ion [M+Na]$^+$;
empirical formula: C$_{11}$H$_{13}$N$_2$O$_4$Cl$_3$NaS$_2$
m/z theoretical: 428.9280
m/z found: 428.9283

3'-Deoxythymidin-3'-yl 4-nitrophenyl disulfide 3

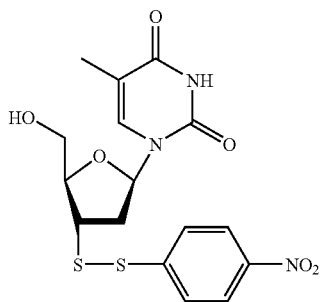

Protocol A1
3'-Deoxy-3'-(2-(trimethylsilyl)ethyl)thiothymidine 1 (300 mg; 0.84 mmol)
Anhydrous dichloromethane (5 ml)
4-nitrobenzenesulfenyl chloride (476 mg, 2.5 mmol)
3 (0.331 g, 0.80 mmol, 96%) in the form of a pale yellow powder.
$^1$H NMR (400 MHz, CDCl$_3$) δ 8.48 (1 H, s, NH), 8.20 (2 H, d, Ar), 7.70 (2 H, d, Ar) 7.46 (1 H, s, 6-H), 6.07 (1 H, dd, J=5.2 Hz, J=11.6 Hz, 1'-H), 4.05 (1 H, m, 5'-H), 4.02 (1 H, m, 4'-H), 3.88 (1 H, m, 5'-H×2), 3.50 (1 H, m, 3'-H), 2.60-2.51 (2 H, m, 2'-H×2), 1.89 (3H, s, 5-CH$_3$) .
$^{13}$C NMR (100 MHz, CDCl$_3$) δ 163.4 (C2), 150.1 (C4), 145.6 (C—NO$_2$), 136.8 (C6), 136.6 (C—SS), 126.1 (2 C Ar), 124.3 (2 C Ar), 111.1 (C5), 85.9 (C1'), 84.7 (C4'), 61.2 (5'-CH$_2$), 45.8 (C3'), 37.6 (2'-CH$_2$), 12.5 (5-CH$_3$) .
MS (DCI, NH$_3$-isobutane): m/z 412 [M+H]$^+$, 429 [M+H+NH$_3$]$^+$, 127 [thymine+H]$^+$.

3'-Deoxythymidin-3'-yl 2-nitrophenyl disulfide 4

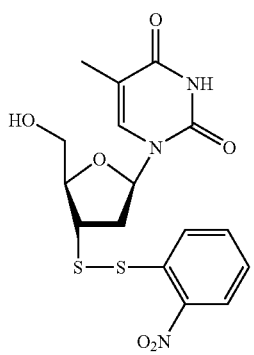

Protocol B1
3'-Deoxy-3'-(2-(trimethylsilyl)ethyl)thiothymidine 1 (300 mg, 0.84 mmol)
2-nitrobenzenesulfenyl chloride (476 mg, 2.5 mmol)
4 (0.314 g, 0.76 mmol, 91%) in the form of a bright yellow powder $^1$H NMR (400 MHz, CDCl$_3$) δ 9.26 (1 H, s, NH), 8.29 (1 H, m, Ar), 8.25 (1H, m, Ar), 7.74 (1 H, m, Ar), 7.52 (1 H, s, 6-H), 7.42 (1 H, m, Ar), 6.04 (1 H, dd, J=4.8 Hz, J=11.6 Hz, 1'-H), 4.08-4.05 (2 H, m, 4'-H and 5'-H), 3.85 (1 H, m, 5'-H), 3.50 (1 H, m, 3'-H), 2.56-2.44 (2 H, m, 2'-H), 1.89 (3 H, s, 5-CH$_3$).
$^{13}$C NMR (100 MHz, CDCl$_3$) δ 163.9 (C2), 150.3 (C4), 145.6 (C—NO$_2$); 136.8 (C6), 136.6 (C—SS), 134.3, 127.1, 126.8, 126.3 (4 C Ar), 110.8 (C5), 85.9 (C1'), 85.0 (C4'), 61.1 (5'-CH$_2$), 45.3 (C3'), 37.8 (2'-CH$_2$), 12.4 (5-CH$_3$).
MS (DCI, NH$_3$-isobutane): m/z 412 [M+H]$^+$, 429 [M+H+NH$_3$]$^+$, 127 [thymine+H]$^+$.

2'-Deoxyuridin-2'-yl trichloromethyl disulfide 7

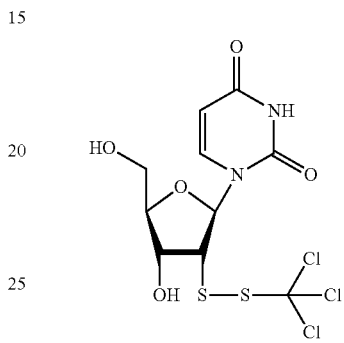

Protocol C2
2'-Deoxy-2'-(2-(trimethylsilyl)ethyl)thiouridine 5 (50 mg, 0.14 mmol)
Anhydrous methanol (1.5 ml)
Trichloromethanesulfenyl chloride (44 µl, 0.42 mmol) 7 (48 mg, 0.12 mmol, 84%) in the form of a white powder.
$^1$H NMR (400 MHz, MeOD), δ 8.01 (1 H, d, J=8 Hz, 6-H), 6.38 (1 H, d, J=8.8 Hz, 1'-H), 5.78 (1 H, d, J=8 Hz, 5-H), 4.54 (1 H, m, 3'-H), 4.25 (1 H, dd, J=5.6 Hz, J=8.8 Hz, 2'-H), 4.09 (1 H, m, 1'-H), 3.78 (2 H, m, 5'-H×2).
$^{13}$C NMR (100 MHz, MeOD) δ 164.4 (C2), 151.1 (C4), 141.0 (C6), 102.2 (C5), 100.2 (C—Cl$_3$), 88.6 (C1'), 87.3 (C4'), 72.8 (C3'), 61.6 (5'-CH$_2$), 59.0 (C2').
MS (DCI, NH$_3$-isobutane): m/z 411 [M+H]$^+$.

2'-Deoxycytidin-2'-yl trichloromethyl disulfide 8

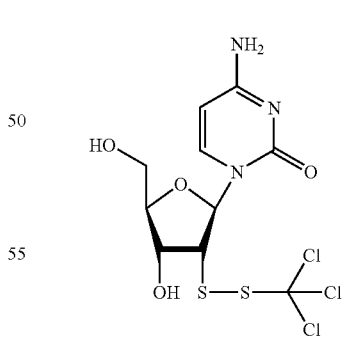

Protocol C2
2'-Deoxy-2'-(2-(trimethylsilyl)ethyl)thiocytidine 6 (40 mg, 0.11 mmol)
Anhydrous methanol (1 ml)
Trichloromethanesulfenyl chloride (38 µl, 0.33 mmol)
8 (53 mg, 0.13 mmol, 86%) in the form of a white powder.
$^1$H NMR (400 MHz, MeOD) δ 7.99 (1 H, d, J=7.6 Hz, 6-H), 6.43 (1 H, d, J=8.8 Hz, 1'-H), 5.78 (1 H, d, J=7.6 Hz, 5-H), 4.55 (1 H, m, 3'-H), 4.25 (1 H, dd, J=5.2 Hz, J=8.8 Hz, 2'-H), 4.09 (1 H, m, 1'-H), 3.78 (2 H, m, 5'-H×2).

$^{13}$C NMR (100 MHz, MeOD) δ 165.8 (C4), 156.8 (C2), 141.9 (C6), 100.3 (C—Cl$_3$), 95.6 (C5), 89.7 (C1'), 87.1 (C4' 72.8 (C3'), 61.7 (5'-CH$_2$), 59.5 (C2').

MS (DCI, NH$_3$-isobutane): m/z 410 [M+H]$^+$.

2'-Deoxyuridin-2'-yl 4-nitrophenyl disulfide 9

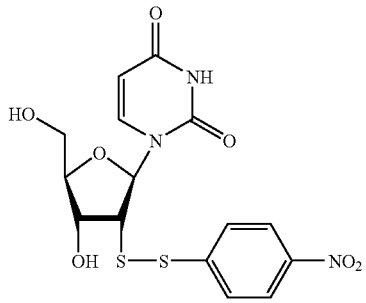

Protocol A2

2'-Deoxy-2'-(2-(trimethylsilyl)ethyl)thiouridine 5 (400 mg, 1.11 mmol)

Anhydrous methanol (8 ml)

4-Nitrobenzenesulfenyl chloride (632 mg, 3.33 mmol)

9 (421 mg, 1.02 mmol, 92%) in the form of a pale yellow powder.

$^1$H NMR (400 MHz, MeOD) δ 8.18 (2 H, d, Ar), 7.78 (1 H, d, J=8.2 Hz, 6-H), 7.66 (2 H, d, Ar), 6.35 (1 H, d, J=9.2 Hz, 1'-H), 5.56 (1 H, d, J=8.4 Hz, 5-H), 4.48 (1 H, m, 3'-H), 4.02 (1 H, m, 4'-H), 3.79 (1 H, m, 2'-H), 3.70 (2 H, m, 5'-H×2).

$^{13}$C NMR (100 MHz, MeOD) δ 163.9 (C2), 150.8 (C4), 146.5 (C—NO$_2$), 145.7 (C—SS), 140.6 (C6), 125.9 (2 C, Ar), 123.7 (2 C, Ar), 101.9 (C5), 87.9 (C1'), 86.8 (C4' 72.9 (C3'), 61.5 (C2'), 60.1 (5'-CH$_2$).

MS (DCI, NH$_3$-isobutane): m/z 414 [M+H]$^+$, 431 [M+H+ NH$_3$].

2'-Deoxycytidin-2'-yl 4-nitrophenyl disulfide 10

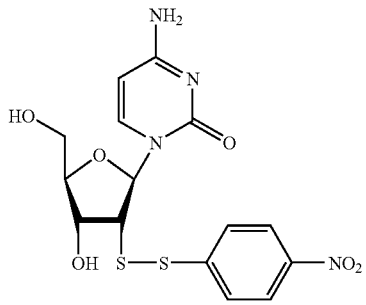

Protocol A2

2'-Deoxy-2'-(2-(trimethylsilyl)ethyl)thiocytidine 6 (200 mg, 0.56 mmol)

Anhydrous methanol (6 ml)

4-Nitrobenzenesulfenyl chloride (316 mg, 1.66 mmol)

10 (158 mg, 0.38 mmol, 69%) obtained after recrystallization from methanol (2 ml) in the form of a bright yellow powder.

$^1$H NMR (400 MHz, DMSO) δ 8.13 (2 H, Ar), 7.65 (2 H, Ar) 7.60 (1 H, d, J=7.6 Hz, 6-H), 7.16 (2 H, bs, 2 NH), 6.27 (1 H, d, J=9.2 Hz, 1'-H), 6.13 (1 H, d, J=5.2 Hz, 3'-OH), 5.57 (1 H, d, J=7.6 Hz, 5-H), 5.05 (1 H, t, J=5.2 Hz, 5'-OH), 4.33 (1 H, m, 3'-H), 3.89 (1 H, m, 4'-H), 3.70 (1 H, m, 2'-H), 3.51 (2 H, bs, 5'-H×2).

$^{13}$C NMR (100 MHz, DMSO) δ 165.7 (C4), 150.1 (C2), 146.3 (C—NO$_2$), 146.1 (C—SS), 141.6 (C6), 126.2 (2 C Ar), 124.4 (2 C Ar), 95.1 (C5), 88.6 (C1'), 86.7 (C4'), 72.7 (C3'), 61.8 (5'-CH$_2$), 59.7 (C2').

MS (FAB+, NAB): m/z 413 [M+H]$^+$.

Cysteine 4-nitrophenyl disulfide 61

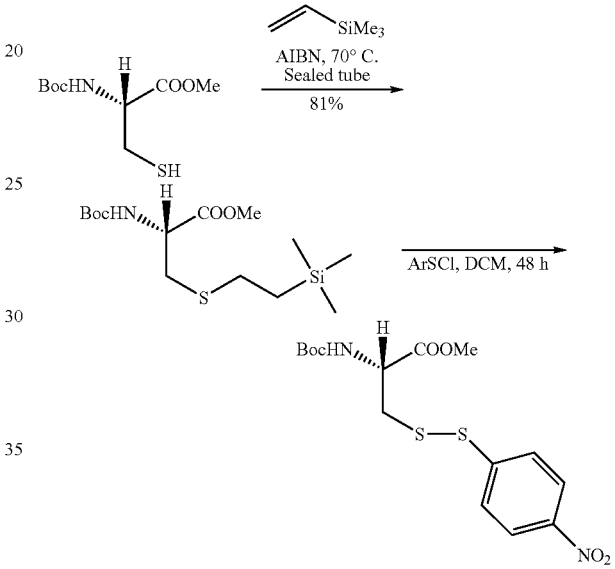

Silylated sulfide in the cysteine series 60

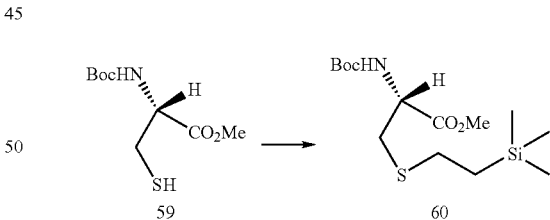

A solution of protected cysteine derivative 59 (1 g, 4.25 mmol) and of trimethylvinylsilane (740 ml, 5.1 mmol) is stirred in the presence of a catalytic amount (10%) of AIBN at 70° C. in a sealed tube for 24 h. The reaction mixture is subsequently evaporated dry to give the compound 60 (1.1 g, 81%) in the form of a light yellow oil.

$^1$H NMR CDCl$_3$ δ 5.40 (1H, d, NH), 4.52 (1H, m, Hα), 3.72 (3H, s, CH$_3$), 2.95 (2H, d, CH$_2$S), 2.52 (2H, m, CH$_2$S), 1.41 (9H, s, (CH$_3$)$_3$), 0.81 (2H, m, CH$_2$Si), 0.12 (9H, s, (CH$_3$)$_3$Si).

$^{13}$C NMR CDCl$_3$ δ 171.5 (C=O), 155.0 (C=O), 79.8 (C Boc), 53.2, 52.3 (2 CH$_2$S), 34.2 (CH), 28.2 (3 CH$_3$ Boc), 17.2 (CH$_2$Si), −1.9 (3 CH$_3$Si).

HRMS for C$_{14}$H$_{29}$NO$_4$NaSSi [M+Na]$^+$, theoretical: 358.1484; found: 358.1483

Cysteine 4-nitrophenyl disulfide 61

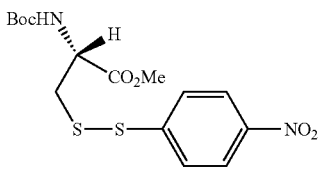

4-Nitrobenzenesulfenyl chloride (177 mg, 0.93 mmol) is added to a solution of silylated cysteine sulfide 60 (100 mg, 0.31 mmol) in anhydrous dichloromethane (5 ml) and then the reaction medium is stirred at ambient temperature under an inert atmosphere for 48 hours. The mixture is subsequently diluted with dichloromethane, washed with water and then evaporated to dryness. The residue is purified by chromatography on silica gel in a cyclohexane/dichloromethane (50-50, then 70-30, then 0-100) mixture to give the compound 61 (79 mg, 69%) in the form of a light yellow oil.

$^1$H NMR CDCl$_3$ δ 8.22 (2H, d, Harom), 7.66 (2H, d, Harom), 5.31 (1H, m, NH), 4.62 (1H, m, Hα), 3.78 (3H, s, CO$_2$CH$_3$), 3.32 (1H, dd, CH$_2$), 3.19 (1H, dd, CH$_2$), 1.46 (9H, s, (CH$_3$)$_3$).

$^{13}$C NMR CDCl$_3$ δ 107.7 (C=O), 154.8 (C=O), 146.4, 145.9 (2C, arom), 126.2, 124.1 (2×2C arom), 80.5 (C(CH$_3$)$_3$), 52.7 (CO$_2$CH$_3$), 41.2 (CH$_2$S), 28.2 (3 CH$_3$).

2-Deoxyuridin-2'-yl 2-nitrophenyl disulfide 11

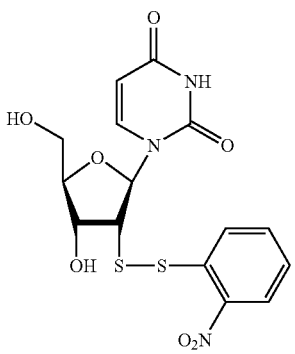

Protocol B2
2'-Deoxy-2'-(2-(trimethylsilyl)ethyl)thiouridine 5
(200 mg, 0.55 mmol)
Anhydrous methanol (4 ml)
2-Nitrobenzenesulfenyl chloride (316 mg, 1.66 mmol)
11 (220 mg, 0.53 mmol, 96%) in the form of a bright yellow powder.

$^1$H NMR (400 MHz, DMSO) δ 11.14 (1 H, s, NH), 8.21 (1 H, m, Ar), 7.79 (1 H, m, Ar), (1 H, d, J=8.1 Hz, 6-H), 7.49 (2 H, m, Ar), 6.23 (1 H, d, J=9.2 Hz, 1'-H), 6.17 (1 H, m, 3'-OH), 5.42 (1 H, d, J=8.0 Hz, 5-H), 5.03 (1 H, m, 3'-H), 4.35 (1 H, m, 5'-OH), 3.91 (1 H, m, 4'-H), 3.69 (1 H, dd, J=5.2 Hz, J=9.1 Hz, 2'-H), 3.51 (2H, m, 5'-H×2).

$^{13}$C NMR (100 MHz, DMSO) δ 162.8 (C2), 151.0 (C4), 145.3 (C—NO$_2$), 145.7 (C—SS), 140.3 (C6), 136.0 (C—SS), 135.3, 127.7, 127.5, 126.40 (4 C, Ar), 102.7 (C5), 87.3 (C1'), 86.9 (C4'), 72.7 (C3'), 61.6 (5'-CH$_2$), 58.3 (C2').

MS (DCI, NH$_3$-isobutane): m/z 414 [M+H]$^+$, 431 [M+H+NH$_3$]$^+$.

2-Deoxycytidin-2'-yl 2-nitrophenyl disulfide 12

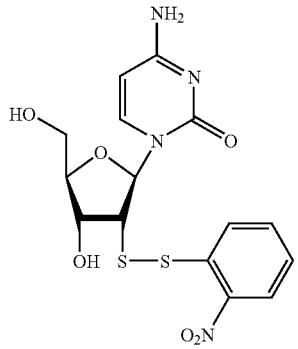

Protocol B2
2'-Deoxy-2'-(2-(trimethylsilyl)ethyl)thiocytidine 6
(100 mg, 0.28 mmol)
Anhydrous methanol (4 ml)
4-Nitrobenzenesulfenyl chloride (158 mg, 0.83 mmol)
12 (43 mg, 0.10 mmol, 42%) in the form of a bright yellow powder.

$^1$H NMR (400 MHz, MeOD) δ 8.21 (2 H, m, Ar), 7.73 (2 H, m, Ar+6-H, J=7.5 Hz), 7.44 (1 H, m, Ar), 6.42 (1 H, d, J=9.3 Hz, 1'-H), 5.70 (1 H, d, J=7.4 Hz, 5-H), 4.47 (1 H, m, 3'-H), 4.03 (1 H, bs, 4'-H), 3.70-3.62 (3 H, m, 5'-H×2+2'-H).

$^{13}$C NMR (100 MHz, MeOD) δ 165.1 (C4), 157.4 (C2), 145.3 (C—NO$_2$), 141.3 (C6), 135.9 (1 C Ar), 145.3 (C—SS), 127.0, 126.6, 125.5 (3 C Ar), 96.1 (C5), 88.8 (C1'), 86.9 (C4'), 72.7 (C3'), 61.6 (5'-CH$_2$), 59.2 (C2').

MS (FAB+, NAB): m/z 413 [M+H]$^+$.

The experimental part below describes the synthetic protocols followed in order to obtain mixed disulfides of formula (III) obtained according to the invention by the process which forms the subject matter of example 2.

3'-Deoxythymidin-3'-yl propyl disulfide 13

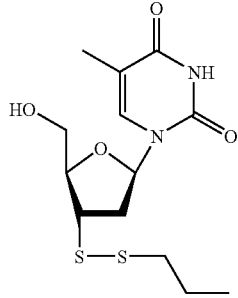

Propane disulfide (108 μl, 0.70 mmol) and then cyanogen bromide (73 mg, 70 mmol) are added to a solution, in anhydrous dichloromethane (3 ml), of silylated nucleoside 1 (50 mg, 0.14 mmol), compound (IIa) as obtained according to the invention. The mixture is left stirring under argon at 40° C. for 96 h. The symmetrical disulfide gradually appears in the form of a beige precipitate, while the second product remains in solution. After hydrolysis with a phosphate buffer solution (0.5M, pH 7, 2 ml) for 30 min, the solvents are evaporated to dryness. The residue obtained is chromatographed on silica gel with a dichloromethane-methanol (95:5) mixture. The mixed disulfide is obtained in the form of a white powder (18 mg, 0.05 mmol, 39%). The symmetrical disulfide 34 is thus obtained in the form of a white powder (8 mg, 0.015 mmol, 22%).

Propane disulfide (131 µl, 0.42 mmol) and then dibromine in solution in dichloromethane (209 µl, 2M, 0.84 mmol) are added to a solution, in anhydrous dichloromethane (4 ml), of silylated nucleoside 1 (30 mg, 0.08 mmol). The mixture is left stirring and under argon for 6 h. A 5% sodium thiosulfate solution is added. The organic phase is washed twice with water (5 ml) and then the organic phases are combined in order to be dried over magnesium sulfate and evaporated to dryness. The residue obtained is chromatographed on silica gel with a dichloromethane-methanol (98:2 and then 95:5) mixture. The symmetrical disulfide 13 is thus obtained in the form of a white powder (8 mg, 0.02 mmol, 28%).

$^1$H NMR (400 MHz, CDCl$_3$) δ 9.11 (1 H, s, NH), 7.56 (1 H, s, 6-H), 6.12 (1 H, dd, J=4.4 Hz, J=6.8 Hz, 1'-H), 4.09-4.01 (2 H, m, 4'-H and 5'-H), 3.90 (1 H, m, 5'-H), 3.60 (1 H, m, 3'-H), 2.73 (2 H, m, CH$_2$—S), 2.72-2.53 (2 H, m, CH$_2$×2), 1.95 (5-CH$_3$), 1.73 (2 H, m, S—CH$_2$—CH$_2$), 1.04 (2 H, m, CH$_2$—CH$_3$).

$^{13}$C NMR (100 MHz, CDCl$_3$) δ 163.2 (C2), 151.2 (C4), 136.5 (C6), 110.8 (C5), 85.9 (C1'), 85.4 (C4'), 61.5 (5'-CH$_2$), 45.2 (C3'), 39.8 (CH$_2$—S), 38.1 (2'-CH$_2$), 22.5 (CH$_2$—CH$_3$), 13.0 (CH$_2$—CH$_3$), 12.5 (5-CH$_3$).

The experimental part below describes the synthetic protocols followed in the preparation of mixed disulfides obtained according to the invention by the process which forms the subject matter of example 3.

2',3'-Didehydro-2',3'-dideoxythymidin-2'-yl trichloromethyl disulfide 15

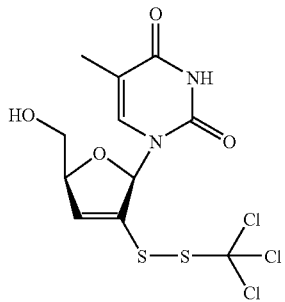

Protocol C3
2',3'-Didehydro-2',3'-dideoxy-2'-(2-(trimethyl-silyl)ethyl) thiothymidine 14 (50 mg, 0.14 mmol)
Anhydrous dichloromethane (3 ml)
Trichloromethanesulfenyl chloride (45 µl, 0.42 mmol)
15 (36 mg, 0.09 mmol, 63%) in the form of a white powder.
$^1$H NMR (400 MHz, CDCl$_3$) δ 7.43 (1 H, bs, 6-H), 7.05 (1 H, m, 1'-H), 6.62 (1 H, m, 3'-H), 5.99 (1 H, m, 4'-H), 3.92 (1 H, dd, J=2.4 Hz, J=12.4 Hz, 5'-H), 3.82 (1 H, dd, J=2.8 Hz, J=12.4 Hz, 5'-H), 1.94 (3 H, s, 5-CH$_3$).
$^{13}$C NMR (100 MHz, CDCl$_3$) δ 162.7 (C2), 150.8 (C4), 135.24 (C3'), 135.16 (C6), 131.8 (C2'), 110.6 (C5), 100.1 (C—Cl$_3$), 91.4 (C1'), 86.8 (C4'), 63.3 (5'-CH$_2$), 13.1 (5-CH$_3$).
MS (DCI, NH$_3$-isobutane): m/z 407 [M+H]$^+$.

2',3'-Didehydro-2',3'-dideoxythymidin-2'-yl 4-nitrophenyl disulfide 16

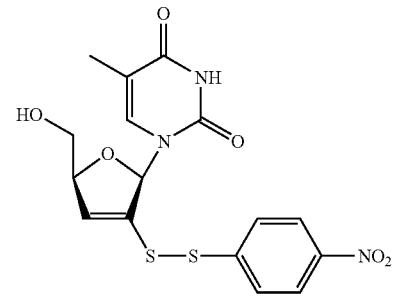

Protocol A1
2',3'-Didehydro-2',3'-dideoxy-2'-(2-(trimethylsilyl)ethyl) thiothymidine 14 (50 mg, 0.14 mmol)
Anhydrous dichloromethane (3 ml)
4-Nitrobenzenesulfenyl chloride (80 mg, 0.42 mmol)
16 (32 mg, 0.08 mmol, 56%) in the form of a yellow powder
$^1$H NMR (400 MHz, CDCl$_3$) δ 8.18 (2 H, m, Ar), 7.60 (2 H, m, Ar), 7.35 (1 H, s, 6-H), 6.91 (1 H, bs, 1'-H), 6.39 (1 H, bs, 3'-H), 4.92 (1 H, bs, 4'-H), 3.84 (1 H, m, 5'-H), 3.73 (1 H, m, 5'-H), 1.83 (3 H, s, 5-CH$_3$).
$^{13}$C NMR (100 MHz, CDCl$_3$) δ 162.5 (C2), 150.7 (C4), 146.7 (C—NO$_2$), 144.2 (C—SS), 135.1 (C6), 133.1 (C2'), 132.4 (C3'), 126.7 (2 C, Ar), 124.2 (2 C, Ar), 102.5 (C5), 91.2 (C1'), 86.9 (C4'), 63.2 (5'-CH$_2$), 13.1 (5-CH$_3$).
MS (DCI, NH$_3$-isobutane): m/z 432 [M+Na]$^+$.

2',3'-didehydro-2',3'-dideoxythymidin-2'-yl 2-nitrophenyl disulfide 17

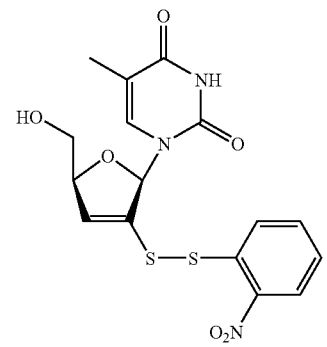

Protocol B3
2',3'-Didehydro-2',3'-dideoxy-2'-(2-(trimethyl-silyl)ethyl) thiothymidine 14 (50 mg, 0.14 mmol)
Anhydrous dichloroethane (3 ml)
4-Nitrobenzenesulfenyl chloride (80 mg, 0.42 mmol)
17 (30 mg, 0.07 mmol, 53%) in the form of a bright yellow powder.
$^1$H NMR (400 MHz, CDCl$_3$) δ 8.30 (1 H, m, Ar), 8.01 (1 H, m, Ar), 7.70 (1 H, m, Ar), 7.44 (1 H, m, Ar), 7.28 (1 H, bs, 6-H), 7.43 (1 H, m, Ar), 6.81 (1 H, m, 1'-H), 6.30 (1 H, m, 3'-H), 4.90 (1 H, m, 4'-H), 3.81 (1H, dd, J=2.8 Hz, J=12.4 Hz, 5'-H), 3.69 (1 H, m, dd, J=3.2 Hz, J=12.4 Hz, 5'-H), 1.86 (3H, s, 5-CH$_3$).

$^{13}$C NMR (100 MHz, CDCl$_3$) δ 162.3 (C2), 150.7 (C4), 145.2 (C—NO$_2$), 135.3 (C—SS), 135.1 (C6), 134.4 (1 C, Ar), 132.7 (C3'), 131.9 (C2'), 127.1, 126.9, 126.1 (3 C, Ar), 110.4 (C5), 89.9 (C1'), 86.9 (C4'), 63.3 (5'-CH$_2$), 13.0 (5-CH$_3$).

MS (DCI, NH$_3$-isobutane): m/z 410 [M+H]$^+$.

2',3'-Didehydro-2',3'-dideoxyuridin-2'-yl trichloromethyl disulfide 20

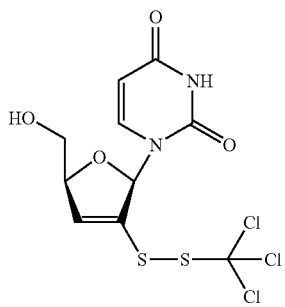

Protocol C3

2',3'-Didehydro-2',3'-dideoxy-2'-(2-(trimethyl-silyl)ethyl)thiouridine 18 (50 mg, 0.15 mmol)

Anhydrous dichloromethane (3 ml)

Trichloromethanesulfenyl chloride (48 µl, 0.44 mmol)

20 (55 mg, 0.14 mmol, 96%) in the form of a white powder.

$^1$H NMR (400 MHz, CDCl$_3$) δ 9.23 (1 H, s, NH), 7.75 (1 H, d, J=8 Hz, 6-H), 7.15 (1 H, m, 1'-H), 6.68 (1 H, m, 3'-H), 5.74 (1 H, d, J=8 Hz, 5-H), 5.04 (1 H, m, 4'-H), 3.97 (1 H, dd, J=2.4 Hz, J=12.8 Hz, 5'-H), 3.84 (1 H, dd, J=2.4 Hz, J=12.4 Hz, 5'-H).

$^{13}$C NMR (100 MHz, CDCl$_3$) δ 164.6 (C2), 150.6 (C4), 141.2 (C6), 136.0 (C3'), 131.3 (C2'), 102.9 (C5), 99.9 (C—Cl$_3$), 90.0 (C1'), 87.4 (C4'), 62.9 (5'-CH$_2$).

MS (DCI, NH$_3$-isobutane): m/z 393 [M+H]$^+$.

2',3'-Didehydro-2',3'-dideoxyuridin-2'-yl 4-nitrophenyl disulfide 21

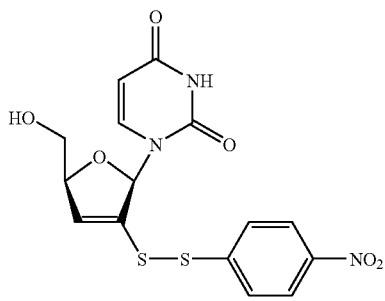

Protocol A1

2',3'-Didehydro-2',3'-dideoxy-2'-(2-(trimethyl-silyl)ethyl)thiouridin 18 (200 mg, 0.58 mmol)

Anhydrous dichloromethane (6 ml)

4-Nitrobenzenesulfenyl chloride (333 mg, 1.75 mmol)

21 (152 mg, 0.38 mmol, 66%) in the form of a yellow powder.

$^1$H NMR (400 MHz, CDCl$_3$) δ 9.40 (1 H, s, NH), 8.16 (2 H, m, Ar), 7.65 (1 H, d, J=8.0 Hz, 6-H), 7.60 (2 H, m, Ar), 7.04 (1 H, m, 1'-H), 6.48 (1 H, m, 3'-H), 5.70 (1H, d, J=8.4 Hz, 5-H), 4.99 (1 H, bs, 4'-H), 3.94 (1 H, m, 5'-H), 3.83 (1 H, m, 5'-H).

$^{13}$C NMR (100 MHz, CDCl$_3$) δ 162.9 (C2), 150.3 (C4), 146.8 (C—NO$_2$), 143.9 (C—SS), 140.8 (C6), 135.1 (C2'), 131.8 (C3'), 126.6 (2 C, Ar), 126.3 (2 C, Ar), 102.8 (C5), 89.7 (C1'), 87.0 (C4'), 63.0 (5'-CH$_2$).

MS (DCI, NH$_3$-isobutane): m/z 396 [M+H]$^+$, 413 [M+NH$_3$]$^+$.

The stage below illustrates the preparation, from the disulfide 21, of the alkylated thiol 31, 2',3'-didehydro-2',3'-dideoxy-2'-methylthiouridine, obtained after in situ formation of the corresponding unstable vinyl thiol.

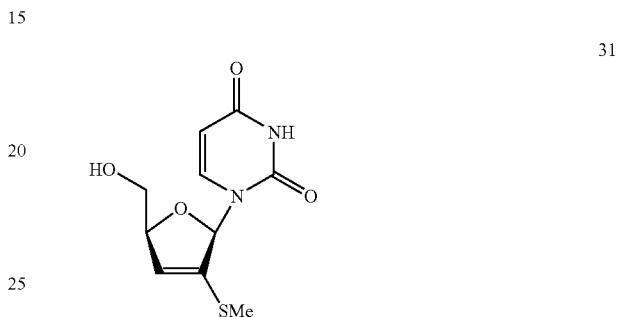

DTT (59 mg, 0.38 mmol) is added to a solution of 21 (30 mg, 0.08 mmol) in anhydrous methanol degassed beforehand with argon. The solution is kept stirred for 30 minutes and then NH$_4$HCO$_3$ (30 mg, 0.38 mmol) and methyl iodide (190 µl, 3.0 mmol) are successively added. After stirring for 1 hour, the reaction mixture is evaporated and then the residue is chromatographed on silica gel in a dichloromethane-methanol (95:5) mixture. The methylated unsaturated compound 31 is obtained in the form of a white foam (16 mg, 0.06 mmol, 82%).

$^1$H NMR (400 MHz, CDCl$_3$) δ 7.60 (1 H, d, J=8 Hz, 6-H), 6.93 (1 H, m, 1'-H), 5.76 (1 H, s, 3'-H), 5.73 (1 H, d, J=7.6 Hz, 5-H), 4.99 (1 H, m, 4'-H), 3.94-3.76 (2 H, m, J=3.2 Hz, J=11.6 Hz, 5'-H×2), 2.41 (Me).

$^{13}$C NMR (100 MHz, CDCl$_3$) δ 162.8 (C2), 150.5 (C4), 141.8 (C6), 136.4 (C3'), 122.3 (C2'), 102.8 (C5), 90.2 (C1'), 87.2 (C4'), 63.6 (5'-CH$_2$), 15.1 (Me).

HRMS calculated for C$_{10}$H$_{12}$N$_2$O$_4$SNa: [M+Na]$^+$ 279.0416, found: 279.0416.

2',3'-Didehydro-2',3'-dideoxyuridin-2'-yl 2-nitrophenyl disulfide 22

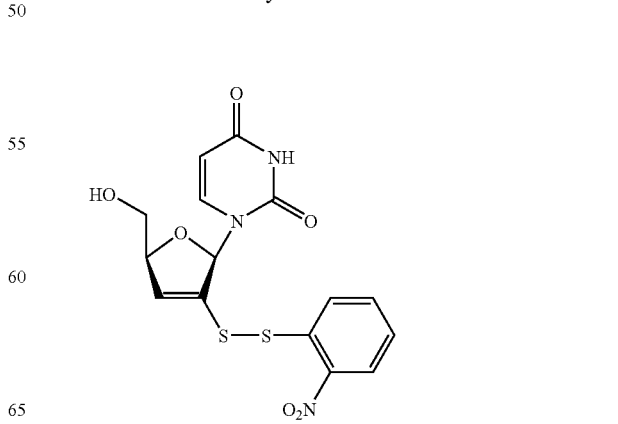

Protocol B3

2',3'-Didehydro-2',3'-dideoxy-2'-(2-(trimethyl-silyl)ethyl) thiouridine 18 (100 mg, 0.29 mmol)

Anhydrous dichloroethane (3 ml)

2-Nitrobenzenesulfenyl chloride (166 mg, 0.88 mmol)

22 (82 mg, 0.21 mmol, 71%) in the form of a bright yellow powder.

$^1$H NMR (400 MHz, CDCl$_3$) δ 8.31 (2 H, m, NH+Ar), 8.02 (1 H, m, Ar), 7.68 (2 H, m, Ar, J=8.0 Hz, 6-H), 7.43 (1 H, m, Ar), 6.98 (1 H, m, 1'-H), 6.40 (1 H, m, 3'-H), 5.66 (1 H, d, J=8.4 Hz, 5-H), 4.97 (1 H, m, 4'-H), 3.94-3.77 (2 H, m, 5'-H×2).

$^{13}$C NMR (100 MHz, CDCl$_3$) δ 162.6 (C2), 150.1 (C4), 145.4 (C—NO$_2$), 140.7 (C6), 135.1 (C—SS), 134.3 (1 C, Ar), 133.1 (C3'), 132.4 (C2'), 127.0, 126.9, 126.2 (3 C, Ar), 102.8 (C5), 89.9 (C1'), 87.0 (C4'), 63.1 (5'-CH$_2$).

MS (DCI, NH$_3$-isobutane): m/z 396 [M+H]$^+$, 413 [M+NH$_3$]$^+$.

The experimental part below describes the synthetic protocols followed in order to obtain thiosulfinates of formula (IV) obtained according to the invention by the process which forms the subject matter of example 4.

Thiosulfinate 25

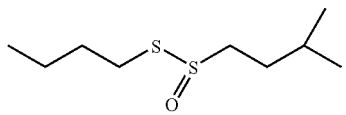

The sulfenyl chloride 24 (203 mg, 1.3 mmol) and tetrabutylammonium fluoride (0.5M solution/MeOH, 105 µl, 0.2 eq.) are successively added to a solution of silylated sulfide 23 (50 mg, 0.26 mmol) in anhydrous dichloroethane (1 ml) and under argon. The reaction mixture is stirred at ambient temperature for 15 h and then heated at reflux for 4 h, and concentrated to give the thiosulfinate 25 in the form of an orangey oil. NMR shows only the presence of thiosulfinate and no longer shows silylated sulfide. The product is characterized without specific purification.

$^1$H NMR (400 MHz, CDCl$_3$) δ 3.00 (2H, t, CH$_2$S), 1.60 (2H, m, CH$_2$), 1.35 (2H, m, CH$_2$), 0.84 (3H, m, CH$_3$).

$^{13}$C NMR (100 MHz, CDCl$_3$) δ 61.1 (CH$_2$SO), 38.3 (CH$_2$S), 34.3 (CH$_2$), 32.6 (CH$_2$), 31.9 (CH$_2$), 27.0 (CH), 22.1 (CH$_3$), 22.0 (CH$_3$×2).

MS (DCI/NH$_3$-isobutane): m/z 215 [M+H], 232 [M+NH$_3$], 248 [M+2NH$_3$].

Thiosulfinate 27

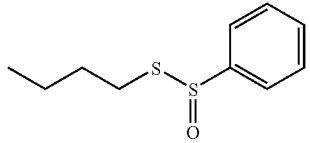

The sulfenyl chloride 26 (83 mg, 0.52 mmol) is added to a solution of silylated sulfur 23 (50 mg, 0.26 mmol) in anhydrous dichloroethane (1 ml) and under argon. The reaction mixture is stirred at ambient temperature for 15 h and then concentrated to give the thiosulfinate 27 in the form of a brown oil. NMR shows only the presence of thiosulfinate and no longer shows silylated sulfide. The product is characterized without specific purification.

$^1$H NMR (400 MHz, CDCl$_3$) δ 8.00-7.30 (5H, m, Ar), 3.00 (2H, t, CH$_2$S), 1.60 (2H, m, CH$_2$), 1.35 (2H, m, CH$_2$), 0.84 (3H, m, CH$_3$).

$^{13}$C NMR (100 MHz, CDCl$_3$) δ 143.0, 136.6, 129.4, 127.5, 35.7 (CH$_2$S), 30.6 (CH$_2$), 21.6 (CH$_2$), 13.4 (CH$_3$).

MS (DCI/NH$_3$-isobutane): m/z 209 [M+H], 225 [M+NH$_3$], 242 [M+2NH$_3$].

The experimental part below describes the synthetic protocols followed in order to obtain thiosulfinates of formula (V) obtained according to the invention by the process which forms the subject matter of example 5.

Thiosulfinate 29

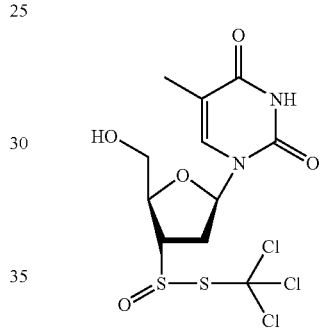

Trichloromethanesulfenyl chloride (56 mg, 0.30 mmol) is added to a solution of silylated sulfide 28 (43 mg, 0.11 mmol) in anhydrous dichloroethane (1 ml) and under argon. The reaction mixture is brought to reflux for 48 hours and then concentrated under a hood under a stream of nitrogen. The residue is chromatographed on silica gel in a dichloromethane-methanol (95:5) mixture. Two products which cannot be separated by chromatography are obtained in the form of a white powder (27 mg, 55%).

Ratio 54 A (disulfide 2)/46 B (thiosulfinate 29)

$^1$H NMR (400 MHz, CDCl$_3$) δ 8.36 (1 H, bs, NH), 8.28 (1 H, bs, NH), 7.47 (1 H, s, 6-H A), 7.22 (1H, s, 6-H B), 6.12 (1 H, m, 1'-H A), 5.87 (1 H, m, 1'-H B), 4.94 (1 H, m, 3'-H B), 4.71 (1 H, m, 4'-H B), 4.29-4.09 (4 H, m, 3'-H A, 4'-H A, 5'-H A, 5'-H B), 3.92-3.84 (2 H, m, 5'-H A, 5'-H B), 3.07-2.91 (2 H, m, 2'-H B×2), 2.80-2.57 (2 H, m, 2'-H A×2), 1.94 (6 H, bs, 5-CH$_3$ A, 5-CH$_3$ B).

$^{13}$C NMR (100 MHz, MeOD) δ 164.9 (C2 A, B), 150.8 (C4 A, B), 136.7 (C6' A), 136.4 (C6' B), 110.8 (C5 A, B), 100.0 (C—Cl$_3$ A, B), 85.5 (C4' A), 85.5 (C1' B), 85.1 (C1' A), 84.7 (C1' A), 79.4 (C4' A), 71.4 (C3' B), 62.1 (5'-CH$_2$), 61.3 (5'-CH$_2$), 48.4 (C3' A), 38.0 (C2' A), 29.3 (C2' B), 11.0 (5-CH$_3$ A, B).

MS (DCI, NH$_3$-isobutane): m/z A 409 [M+H]$^+$, B 441 [M+NH$_3$]$^+$.

Thiosulfinate 30

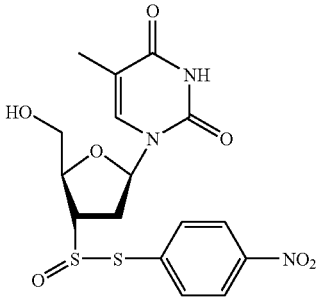

4-Nitrobenzenesulfenyl chloride (56 mg, 0.30 mmol) is added to a solution of silylated sulfide 1 (28 mg, 0.07 mmol) in anhydrous dichloroethane (1 ml) and under argon. The reaction mixture is brought to reflux for 48 hours and then concentrated. The residue is chromatographed on silica gel in a dichloromethane-methanol (95:5) mixture. Two products which cannot be separated by chromatography are obtained in the form of a yellow powder (12 mg, 48%).

Ratio 40 A (thiosulfinate 30)/60 B (disulfide 3)

$^{1}$N NMR (400 MHz, MeOD) δ 8.36 (2 H, d, Ar A), 8.24 (2 H, d, Ar B), 8.05 (2 H, d, Ar A), 7.88 (1H, s, 6-H B), 7.83 (2 H, d, Ar B), 7.18 (1H, s, 6-H A), 6.25 (1 H, m, 1'-H A), 6.13 (1 H, m, 1'-H B), 4.51 (1 H, m, 4'-H A), 4.34 (1 H, m, 3'-H A), 4.01 (1 H, m, 4'-H B), 3.89-4.05 (2 H, m, 5'-H A, 5'-H B), 3.79 (1 H, m, 3'-H B), 3.73 (2 H, m, 5'-H A, 5'-H B), 2.86 (1 H, m, 2'-H A), 2.61-2.42 (3 H, m, 2'-H×2 B, 2'-H A), 1.82 (6 H, bs, 5-CH$_3$ A, 5-CH$_3$ B)

$^{13}$C NMR (100 MHz, MeOD) δ 164.9 (C2 A, B), 150.8 (C4 A, B), 149.7, 146.6, 145.9, 136.9 (C6' B), 136.7, 136.5 (C6'A), 126.1, 124.1, 123.8, 110.4 (C5 A), 109.8 (C5 B), 84.0 (C1' B, C4' B), 84.5 (C1' A), 79.4 (C4' A), 68.8 (C3' A), 61.9 (5-CH$_2$), 60.3 (5'-CH$_2$), 46.0 (C3' B), 37.5 (C2' B), 29.2 (C2' A), 11.0 (5-CH$_3$ A, B).

MS (DCI, NH$_3$-isobutane): m/z A 429 [M+H]$^+$, B 412 [M+H]$^+$.

The experimental part below describes the synthetic protocols followed in order to obtain thiosulfinates of formula (V) obtained according to the invention by the process which forms the subject matter of example 6.

Thiosulfinate 33

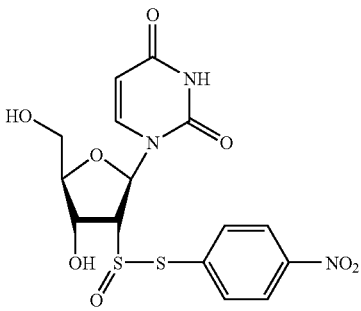

4-Nitrobenzenesulfenyl chloride (30 mg, 0.16 mmol) is added to a solution of silylated sulfoxide 32a (diastereoisomer 1) (20 mg, 0.05 mmol) in an anhydrous methanol-dichloroethane mixture (2 ml, 1:1) and under argon. The reaction mixture is brought to reflux for 48 hours and then concentrated. The residue is chromatographed on silica gel in a dichloromethane-methanol (90:10) mixture. Two products which cannot be separated by chromatography are obtained in the form of a yellow powder (6 mg, 26%).

Ratio 45 (disulfide 9) A/55 (thiosulfinate 33) B $^{1}$H NMR (400 MHz, MeOD) δ 8.44 (2 H, d, Ar B), 8.17 (2 H, d, Ar A), 8.10 (2 H, d, Ar B), 7.90 (1H, d, J=8.0 Hz, 6-H B), 7.77 (1H, d, J=8.4 Hz, 6-H B), 7.66 (2 H, d, Ar A), 6.35 (1 H, d, J=9.2 Hz, 1'-H A), 6.21 (1 H, d, J=9.2 Hz, 1'-H B), 5.65 (1 H, d, J=8.0 Hz, 5-H B), 5.66 (1 H, d, J=8.0 Hz, 5-H A), 4.48 (1 H, m, 3'-H A), 4.34 (1 H, m, 3'-H B), 4.13 (1 H, m, 2'-H B), 4.08 (1 H, m, 4'-H B), 4.04 (1 H, m, 4'-H A), 3.79-3.52 (4 H, m, 2'-H A+5'-H×2 A, 5'-H×2 B).

4-Nitrobenzenesulfenyl chloride (45 mg, 0.24 mmol) is added to a solution of the silylated sulfoxide 32b (diastereoisomer 2) (30 mg, 0.08 mmol) in an anhydrous methanol-dichloroethane mixture (2 ml, 1:1) and under argon. The reaction mixture is brought to reflux for 48 hours and then concentrated. The residue is chromatographed on silica gel in a dichloromethane-methanol (90:10) mixture. Two products which cannot be separated by chromatography are obtained in the form of a yellow powder (12 mg, 35%).

Ratio 37 (disulfide 9) A/63 (thiosulfinate 33) B $^{1}$H NMR (400 MHz, MeOD) δ 8.44 (2 H, d, Ar B), 8.18 (2 H, d, Ar A), 8.11 (2 H, d, Ar B), 7.90 (1H, d, J=8.4 Hz, 6-H B), 7.78 (1H, d, J=8.4 Hz, 6-H B), 7.65 (2 H, d, Ar A), 6.35 (1 H, d, J=9.2 Hz, 1'-H A), 6.21 (1 H, d, J=9.2 Hz, 1'-H B), 5.66 (1 H, d, J=8.0 Hz, 5-H B), 5.66 (1 H, d, J=8.0 Hz, 5-H A), 4.48 (1 H, m, 3'-H A), 4.34 (1 H, m, 3'-H B), 4.13 (1 H, m, 2'-H B), 4.08 (1 H, m, 4'-H B), 4.02 (1 H, m, 4'-H A), 3.79 (1 H, m, 2'-H A), 3.75-3.70 (4 H, m, 5'-H×2 A, 5'-H×2 B).

MS (ES+): m/z A 413 [M+H]$^+$, B 429 [M+H]$^+$.

The experimental part below describes the synthetic protocols followed in order to obtain symmetrical disulfides of formula (VI) obtained according to the invention by the process which forms the subject matter of example 7.

Bis(3'-dideoxythymidin-3'-yl) disulfide 34

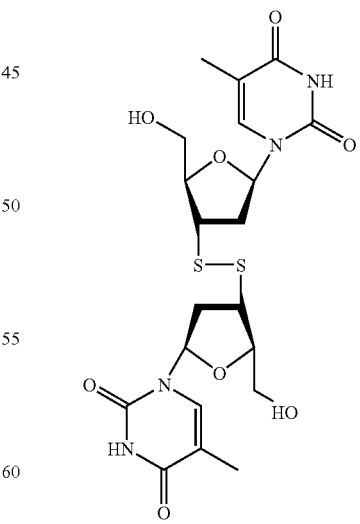

Dibromine in solution in dichloromethane (69 μl, 2M, 0.015 mmol) is added to a solution of silylated nucleoside 1 (10 mg, 0.03 mmol) in anhydrous dichloromethane (4 ml). The mixture is left stirring and under argon for 4 h. A 5% sodium thiosulfate solution is added. The organic phase is washed twice with water (5 ml) and then the organic phases are combined in order to be dried over magnesium sulfate and evaporated to dryness. The residue obtained is chromatographed on silica gel with a dichloromethane-methanol (98:2 then 95:5) mixture. The symmetrical disulfide 34 is thus obtained in the form of a white powder (5 mg, 0.01 mmol, 70%).

Cyanogen bromide (0.06 mg, 0.57 mmol) is added to a solution of silylated nucleoside 1 (40 mg, 0.11 mmol) in anhydrous dichloroethane (3 ml). The mixture is left stirring under argon at 40° C. for 96 h. The symmetrical disulfide gradually appears in the form of a beige precipitate, while the second product remains in solution. After hydrolysis with a phosphate buffer solution (0.5M, pH 7, 2 ml) for 30 min, the solvents are evaporated to dryness. The residue obtained is chromatographed on silica gel with a dichloromethane-methanol (95:5) mixture. The symmetrical disulfide 34 is thus obtained in the form of a white powder (12 mg, 0.02 mmol, 43%).

$^1$H NMR (400 MHz, MeOD) δ 8.59 (1 H, s, NH), 7.54 (1 H, s, 6-H), 6.15 (1 H, dd, J=3.2 Hz, J=7.6 Hz, 1'-H), 4.09-4.06 (1 H, dd, J=2.4 Hz, J=12.0 Hz, 5'H), 3.86 (1 H, m, 4'-H), 3.81 (1H, dd, J=2.4 Hz, J=12.0 Hz, 5'H), 3.55 (1H, m, 3'-H), 2.66-2.41 (2H, m, 2'H×2), 1.92 (5-CH$_3$).

$^{13}$C NMR (100 MHz, MeOD) δ 163.5 (C2), 150.1 (C4), 136.2 (C6), 110.8 (C5), 88.6 (C4'), 85.0 (C1'), 60.6 (5'-CH$_2$), 42.7 (C-3'), 33.7 (2'-CH$_2$), 12.5 (5-CH$_3$).

MS (DCI, NH$_3$-isobutane): m/z 515 [M+H]$^+$.

Bis(5-bromo-2',3'-dideoxyuridin-3'-yl) disulfide 36 and 5-bromo-2',3'-dideoxy-3'-(2-(trimethylsilyl)ethyl)thiouridine 36-1

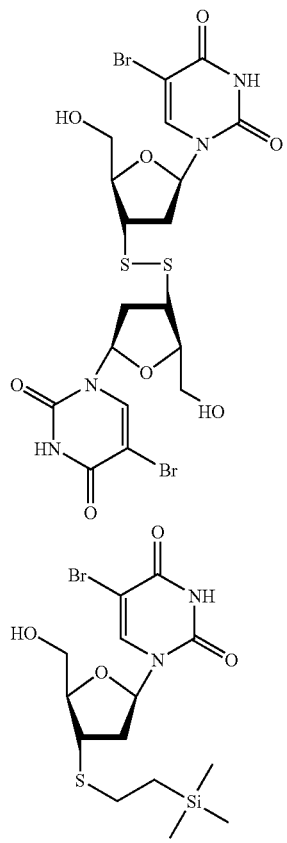

Cyanogen bromide (0.230 mg, 2.17 mmol) is added to a solution of silylated nucleoside 35 (0.150 g, 0.44 mmol) in anhydrous dichloromethane (4 ml). The mixture is left stirring under argon at 40° C. for 96 h. The symmetrical disulfide gradually appears in the form of a beige precipitate, while the second product remains in solution. After hydrolysis with a phosphate buffer solution (0.5M, pH 7, 2 ml) for 30 min, the solvents are evaporated to dryness. The residue obtained is taken up in the minimum amount of dichloromethane in order to be chromatographed on silica gel with a dichloromethane-methanol (98:2 then 95:5) mixture. The symmetrical disulfide 36 is thus obtained in the form of a white powder (27 mg, 0.04 mmol, 21%). The above bromosilylated derivative 36-1 is obtained in the form of a white powder (42 mg, 0.1 mmol, 25%).

Symmetrical disulfide 36

$^1$H NMR (400 MHz, CDCl$_3$) δ 8.63 (1H, s, 6-H), 6.12 (1 H, dd, J=6.5 Hz, J=4.0 Hz, 1'-H), 4.05 (1H, s, 4'-H), 3.97 (1 H, dd, J=2.4 Hz, J=12.3 Hz, 5'-H), 3.86 (1H, dd, J=2.7 Hz, J=12.3 Hz, 5'-H), 3.66 (1 H, m, 3'-H), 2.61 (2 H, m, 2'-H×2).

$^{13}$C NMR (100 MHz, CDCl$_3$) δ 160.3 (C2), 150.1 (C4), 140.7 (C6), 96.3 (C5), 86.2 (C1'), 85.3 (C4'), 60.0 (5'-CH$_2$), 45.3 (2'-C), 38.3 (C3').

MS (FAB+, NBA): m/z=645 [M+H]$^+$.

Bromosilylated Derivative 36-1

$^1$H NMR (400 MHz, CDCl$_3$) δ 8.41 (1H, s, 6-H), 6.09 (1H, dd, J=6.7 Hz, J=3.2 Hz, 1'-H), 4.14 (1H, s, 5'-H), 4.93 (2 H, m, 4'-H and 5'-H), 3.95 (1 H, m, 3'-H), 2.66 (2 H, m, S—CH$_2$), 2.60-2.44 (2 H, m, 2'-H×2), 1.28 (1H, t, 5'-OH), 0.88 (2 H, m, CH$_2$—Si), −0.02 (9 H, s, Si(CH$_3$)$_3$).

$^{13}$C NMR (100 MHz, CDCl$_3$), δ 158.8 (C2), 149.3 (C4), 140.4 (C6), 96.1 (C5), 86.3 (C1'), 86.2 (C4'), 60.8 (5'-CH$_2$), 41.2 (2'-CH$_2$), 39.6 (C3'), 27.6 (S—CH$_2$), 17.5 (CH$_2$—Si), −1.5 (Si (CH$_3$)$_3$).

MS (FAB+, NBA) m/z=423 [M+H]$^+$.

The experimental part below describes the synthetic protocols followed in the preparation of mixed disulfides of formula (III') identified by the references 37-43.

Protocol D 3 (1 equivalent), dissolved beforehand in THF/phosphate buffer degassed beforehand by sparging under argon, is added to a solution of the thiol (10 equivalents) in 5% phosphate buffer (pH=9.5) degassed beforehand by sparging under argon (1 equivalent). The solution is kept stirred and under argon for 2 hours. The solvents are evaporated and the residue is chromatographed on silica gel in a dichloromethane/methanol (95:5) mixture.

Protocol E 3 (1 equivalent), dissolved beforehand in THF/phosphate buffer degassed beforehand by sparging under argon, is added to a solution of the thiol (10 equivalents) in imidazole buffer (10$^{-3}$M, pH=6.0, ionic strength 1M) degassed beforehand by sparging under argon (q.s. for a concentration of 0.5 mol.l$^{-1}$). The solution is kept stirred and under argon for 15 hours. The solvents are evaporated and the residue is chromatographed on silica gel in a dichloromethane-methanol (90:10) mixture.

Protocol F 3 (1 equivalent), dissolved beforehand in THF/phosphate buffer degassed beforehand by sparging under argon, is added to a solution of the thiol (1 equivalent) in imidazole buffer (pH=6.0, ionic strength 1M) degassed beforehand by sparging under argon (1 equivalent). The solution is kept stirred and under argon for 15 hours. Dichloromethane is added and then the organic phase is washed with water (5 ml). The organic phases are combined, dried over magnesium sulfate and evaporated to dryness. The residue is chromatographed on silica gel in a dichloromethane-methanol (90:10) mixture to result in the symmetrical disulfide. The aqueous phase is evaporated to dryness and then the residue is taken up in order to be chromatographed on a reverse phase in a water/methanol (90:10) mixture in order to result in the mixed disulfide.

Allyl 3'-deoxythymidin-3'-yl disulfide 37

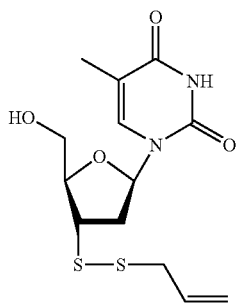

Protocol D
3'-Deoxythymidin-3'-yl 4-nitrophenyl disulfide 3 (70 mg, 0.17 mmol)/10 ml of tetrahydrofuran
Allylthiol (476 µl, 2.5 mmol)/425 µl of phosphate buffer
37 (45 mg, 0.14 mmol, 80%) in the form of a pale yellow oil.
$^1$H NMR (400 MHz, CDCl$_3$) δ 8.56 (1 H, s, NH), 7.53 (1 H, s, 6-H), 6.1 (1 H, dd, J=4.8 Hz, J=6.8 Hz, 1'-H), 5.90-5.81 (1 H, m, H allyl), 5.26-5.20 (2 H, m, 2H allyl), 4.09-4.01 (2 H, m, 4'-H and 5'-H), 3.90 (1 H, m, 5'-H), 3.62 (1 H, m, 3'-H), 3.90 (2 H, m, CH$_2$—S allyl), 2.55 (2 H, m, 2'-H×2), 1.93 (3 H, s, 5-CH$_3$).
$^{13}$C NMR (100 MHz, CDCl$_3$) δ 163.3 (C2), 150.0 (C4), 136.5 (C6), 134.1 (CH-allyl), 117.2 (CH$_2$-allyl), 110.8 (C5), 85.8 (C1'), 85.4 (C4'), 45.2 (C3'), 61.5 (5'-CH$_2$), 38.2 (2'-CH$_2$), 34.7 (CH$_2$—S), 12.5 (5-CH$_3$).
MS (DCI, NH$_3$-isobutane): m/z 331 [M+H]$^+$.

3'-Deoxythymidin-3'-yl 2-hydroxyethyl disulfide 38

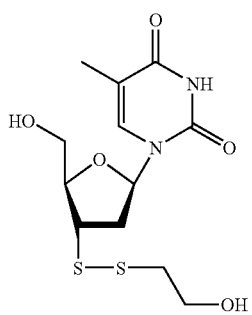

Protocol E
3'-Deoxythymidin-3'-yl 4-nitrophenyl disulfide 3 (100 mg, 0.24 mmol)/2.5 ml of tetrahydrofuran and 2.5 ml of imidazole buffer
Mercaptoethanol (170 µl, 2.43 mmol)/5 ml of imidazole buffer
38 (41 mg, 0.043 mmol, 50%) in the form of a white powder
Bis(3'-dideoxythymidin-3'-yl) disulfide 34 (14 mg, 0.027 mmol, 23%) in the form of a white powder.
$^1$H NMR (400 MHz, CDCl$_3$) δ 8.25 (1 H, s, NH), 7.59 (1 H, s, 6-H), 6.08 (1 H, dd, J=5.2 Hz, J=6.4 Hz, 1'-H), 4.12-4.00 (3 H, m, 4'-H and 5'-H×2), 3.94 (2 H, m, CH$_2$—OH), 3.73 (1 H, m, 3'-H), 3.01-2.93 (2 H, m, CH$_2$—S), 2.54 (2 H, m, 2'-H×2), 1.94 (3 H, s, 5-CH$_3$).

$^{13}$C NMR (100 MHz, CDCl$_3$) δ 165.0 (C2), 150.8 (C4), 136.8 (C6), 109.7 (C5), 85.6 (C4'), 84.5 (C1'), 60.6 (5'-CH$_2$), 59.8 (CH$_2$—OH), 45.4 (C3'), 41.8 (CH$_2$—S), 37.9 (2'-CH$_2$), 11.0 (5-CH$_3$).
MS (DCI, NH$_3$-isobutane): m/z 335 [M+H]$^+$.

2-Aminoethyl 3'-deoxythymidin-3'-yl disulfide hydrochloride 39

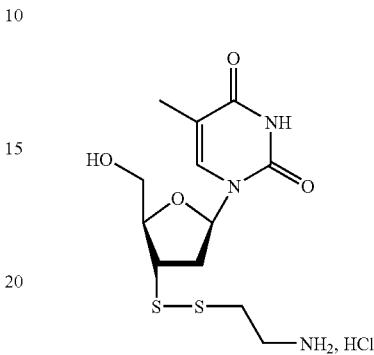

Protocol F
3'-Deoxythymidin-3'-yl 4-nitrophenyl disulfide 3 (50 mg, 0.12 mmol)/2 ml of tetrahydrofuran and 2 ml of imidazole buffer
2-Aminoethanethiol hydrochloride (28 mg, 0.24 mmol)/400 µl of imidazole buffer 39 (9 mg, 0.043 mmol, 20%) in the form of a white powder
Bis(3'-dideoxythymidin-3'-yl) disulfide 34 (15 mg, 0.012 mmol, 48%) in the form of a white powder.
$^1$H NMR (400 MHz, D$_2$O) δ 7.54 (1H, s, 6-H), 6.08 (1 H, dd, J=4.4 Hz, J=7.2 Hz, 1'-H), 4.02 (1 H, m, 4'-H), 3.87 (1 H, dd, J=2.8 Hz, J=12.8 Hz, 5'-H), 3.76 (1 H, dd, J=2.8 Hz, J=12.8 Hz, 5'-H), 3.52 (1H, m, 3'-H), 3.30 (2 H, m, CH$_2$—NH$_2$), 2.93 (2 H, m, CH$_2$—S), 2.60-2.43 (2 H, m, 2'-H×2), 1.80 (3 H, s, 5-CH$_3$).
$^{13}$C NMR (100 MHz, D$_2$O) δ 166.4 (C2), 151.5 (C4), 137.5 (C6), 111.1 (C5), 85.1 (C4'), 84.8 (C1'), 60.5 (5'-CH$_2$), 45.1 (C-3'), 37.8 (CH$_2$—NH$_2$), 36.9 (2'-CH$_2$), 35.0 (CH$_2$—S), 11.5 (5-CH$_3$).
MS (DCI, NH$_3$-isobutane): m/z 335 [M+H]$^+$.

Butyl 3'-deoxythymidin-3'-yl disulfide 40

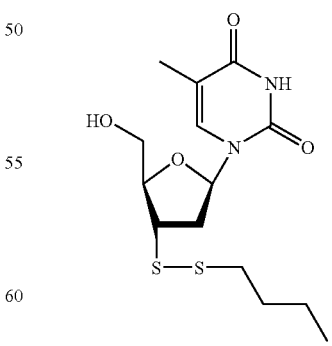

Protocol D
3'-Deoxythymidin-3'-yl 4-nitrophenyl disulfide 3 (40 mg, 0.097 mmol)/6 ml of tetrahydrofuran
Butanethiol (107 µl, 0.97 mmol)/243 µl of phosphate buffer 40 (15 mg, 0.043 mmol, 45%) in the form of a white powder Bis(3'-dideoxythymidin-3'-yl) disulfide 34 (6 mg, 0.012 mmol, 24%) in the form of a white powder.

$^1$H NMR (400 MHz, CDCl$_3$) δ 8.56 (1 H, s, NH), 7.54 (1 H, s, 6-H), 6.12 (1 H, dd, J=4.4 Hz, J=6.8 Hz, 1'-H), 4.10-4.02 (2 H, m, 4'-H and 5'-H), 3.90 (1 H, m, 5'-H), 3.60 (1 H, m, 3'-H), 2.75 (2 H, m, CH$_2$—S), 2.64-2.51 (2H, m, CH$_2$×2), 1.93 (3 H, s, 5-CH$_3$), 1.68 (2 H, m, S—CH$_2$—CH$_2$), 1.43 (2 H, m, CH$_2$—CH$_3$), 0.95 (2 H, m, CH$_2$—CH$_3$).

$^{13}$C NMR (100 MHz, CDCl$_3$) δ 163.3 (C2), 150.0 (C4), 136.5 (C6), 110.8 (C5), 85.8 (C1'), 85.4 (C4'), 61.5 (5'-CH$_2$), 45.2 (C3'), 39.8 (CH$_2$—S), 38.2 (2'-CH$_2$), 31.2 (S—CH$_2$—CH$_2$), 21.5 (CH$_2$—CH$_3$), 13.6 (CH$_2$—CH$_3$), 12.5 (5-CH$_3$).

MS (FAB+, NBA matrix): m/z 347 [M+H]$^+$, 369 [M+Na]$^+$.

3'-Deoxythymidin-3'-yl hexyl disulfide 41

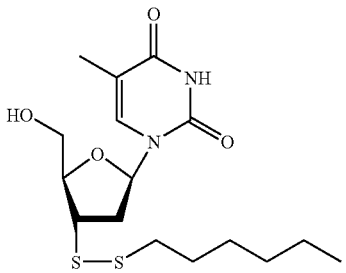

Protocol D

3'-Deoxythymidin-3'-yl 4-nitrophenyl disulfide 3 (34 mg, 0.083 mmol)/6 ml of tetrahydrofuran Hexanethiol (123 μl, 0.83 mmol)/243 μl of phosphate buffer 41 (22 mg, 0.059 mmol, 71%) in the form of a white powder.

$^1$H NMR (400 MHz, CDCl$_3$) δ 8.66 (1 H, s, NH), 7.56 (1 H, s, 6-H), 6.12 (1 H, dd, J=4.7 Hz, J=7.2 Hz, 1'-H), 4.10-4.01 (2 H, m, 4'-H and 5'H), 3.90 (1 H, m, 5'-H), 3.60 (1 H, m, 3'-H), 2.70 (2 H, m, CH$_2$—S), 2.64-2.48 (2 H, m, 2'H×2), 1.92 (3 H, s, 5-CH$_3$), 1.68 (2 H, m, CH$_2$—CH$_2$—S), 1.44-1.25 (6 H, m, CH$_2$—CH$_2$—CH$_2$), 0.91 (3 H, m, CH$_2$—CH$_3$).

$^{13}$C NMR (100 MHz, CDCl$_3$) δ 163.4 (C2), 150.1 (C4), 133.4 (C6), 110.8 (C5), 85.8 (C1'), 85.5 (C4'), 61.5 (5'-CH$_2$), 45.3 (C3'), 40.2 (CH$_2$—S), 38.2 (2'-CH$_2$), 31.3 (1C, CH$_2$), 29.1 (CH$_2$—CH$_2$—S), 28.0, 22.4 (2 C, CH$_2$), 13.9 (CH$_2$—CH$_3$), 12.4 (5-CH$_3$).

MS (DCI, NH$_3$-isobutane): m/z 375 [M+H]$^+$.

3'-Deoxythymidin-3'-yl octyl disulfide 42

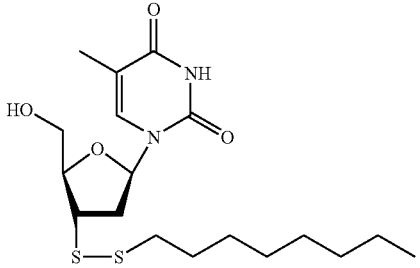

Protocol E

3'-Deoxythymidin-3'-yl 4-nitrophenyl disulfide 3 (75 mg, 0.18 mmol)/2.5 ml of tetrahydrofuran and 2.5 ml of imidazole buffer Octanethiol (316 μl, 1.82 mmol)/5 ml of imidazole buffer 42 (12 mg, 0.030 mmol, 16%) in the form of a white powder Bis(3'-dideoxythymidin-3'-yl) disulfide 34 (30 mg, 0.027 mmol, 65%) in the form of a white powder.

$^1$H NMR (400 MHz, CDCl$_3$) δ 8.66 (1 H, s, NH), 7.68 (1 H, s, 6-H), 6.13 (1 H, dd, J=4.4 Hz, J=6.8 Hz, 1'-H), 4.09-3.88 (3 H, m, 4'-H and 5'H×2), 3.60 (1 H, m, 3'-H), 2.73 (2H, m, CH$_2$—S), 2.74-2.51 (2 H, m, 2'H×2), 1.93 (3 H, s, 5-CH$_3$), 1.68 (2 H, m, CH$_2$—CH$_2$—S), 1.39-1.20 (10 H, m, CH$_2$—CH$_2$—CH$_2$—CH$_2$), 0.90 (3 H, m, CH$_2$—CH$_3$).

$^{13}$C NMR (100 MHz, CDCl$_3$) δ 163.5 (C2), 150.1 (C4), 136.5 (C6), 110.8 (C5), 85.8 (C1'), 85.4 (C4'), 61.4 (5'-CH$_2$), 45.2 (C-3'), 40.1 (CH$_2$—S), 38.1 (2'-CH$_2$), 31.7 (CH$_2$), 29.2 (CH$_2$—CH$_2$—S), 29.1, 28.4, 22.6 (4C, CH$_2$), 14.0 (CH$_2$—CH$_3$), 12.5 (5-CH$_3$).

MS (DCI, NH$_3$-isobutane): m/z 403 [M+H]$^+$.

3'-Deoxythymidin-3'-yl 6-hydroxyhexyl disulfide 43

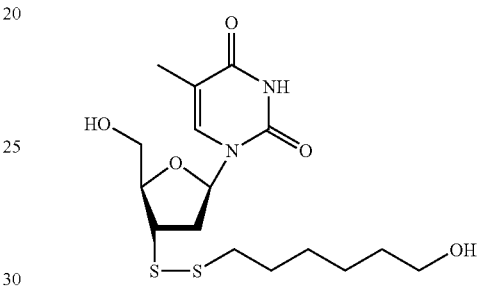

Protocol D

3'-Deoxythymidin-3'-yl 4-nitrophenyl disulfide 3 (55 mg, 0.13 mmol)/6 ml of tetrahydrofuran 6-Mercaptohexanol (183 μl, 1.34 mmol)/334 μl of phosphate buffer 43 (37 mg, 0.094 mmol, 71%) in the form of a white powder.

$^1$H NMR (400 MHz, MeOD) δ 7.94 (1 H, s, 6-H), 6.16 (1 H, dd, J=4.8 Hz, J=6.8 Hz, 1'-H), 4.02-3.92 (2 H, m, 4'-H and 5'H), 3.81 (1 H, m, 5'-H), 3.58 (3 H, m, 3'-H+CH$_2$—OH), 2.79 (2 H, m, CH$_2$—S), 2.62-2.42 (2 H, m, 2'H×2), 1.90 (3 H, s, 5-CH$_3$), 1.74 (2 H, m, CH$_2$—CH$_2$—S), 1.56 (2 H, m, CH$_2$—OH), 1.44 (4 H, m, CH$_2$—CH$_2$).

$^{13}$C NMR (100 MHz, MeOD) δ 162.2 (C2), 150.8 (C4), 136.8 (C6), 109.8 (C5), 85.6 (C4'), 84.5 (C1'), 61.4 (CH$_2$—OH), 60.6 (5'-CH$_2$), 45.4 (C-3'), 39.2 (CH$_2$—S), 38.0 (2'-CH$_2$), 32.0 (CH$_2$—CH$_2$—OH), 28.7 (CH$_2$—CH$_2$—S), 27.8, 25.0 (2 C, CH$_2$), 11.0 (5-CH$_3$).

MS (DCI, NH$_3$-isobutane): m/z 391 [M+H]$^+$.

The experimental part below describes the synthetic protocols followed in order to obtain novel vinyl thiols identified by the reference 44.

Preparation of a vinyl thiol 44 and of a bis(2',3'-didehydro-2',3'-dideoxyuridin-2'-yl) disulfide 45

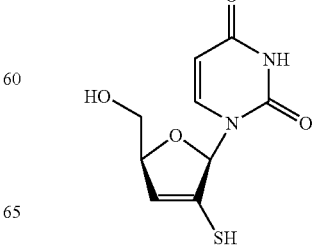

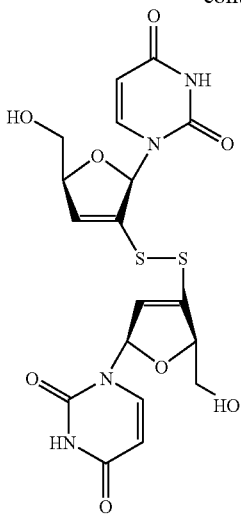

DTT (2.1 mg, 0.03 mmol) is added to a solution of 21 (10 mg, 0.03 mmol) in deuterated methanol. The solution is kept stirred for 15 minutes and then a first proton NMR spectrum is recorded. The rapid formation of a single first product corresponding to the vinyl thiol 44 is observed (as a mixture with 50% of starting compound). The reaction is subsequently monitored by NMR every hour for 4 hours. It reaches a stationary state with a vinyl thiol/starting material (70/30) mixture. A product precipitates at the bottom of the tube. The NMR spectrum of the solution shows the disappearance of the aromatic protons carried by the 4-nitrophenyl group, while that of the precipitate obtained shows only the presence of the aromatic protons.

The tube is subsequently stored at ambient temperature. After leaving overnight, the vinyl thiol has been essentially and completely converted to the corresponding symmetrical disulfide 45.

Vinyl Thiol 44

$^1$H NMR (400 MHz, MeOD) δ 7.90 (1 H, d, J=8.0 Hz, 6-H), 7.06 (1 H, m, 1'-H), 6.55 (1 H, m, 3'-H), 5.72 (1 H, d, J=8.4 Hz, 5-H), 4.93 (1 H, s, 4'-H), 3.73 (2 H, m, 5'-H×2).

Symmetrical Disulfide 45

$^1$H NMR (400 MHz, MeOD) δ 7.88 (1H, d, J=8.0, Hz, 6-H), 6.83 (1 H, m, 1'-H), 6.22 (1 H, m, 3'-H), 5.75 (1 H, d, J=8.0 Hz, 5-H), 4.91 (1 H, s, 4'-H), 3.71 (2 H, m, 5'-H×2).

MS (FAB+, NBA) m/z=242 [M/2+H]$^+$.

The experimental part below illustrates the synthesis of compounds of formulae (IIa) and (IIb) as intermediate compounds.

2',3'-Didehydro-2',3'-dideoxy-2'-(2-(trimethylsilyl)ethyl)thiothymidine 14

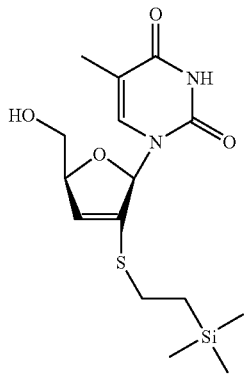

4,4'-Dimethoxytrityl chloride (1.99 g, 5.87 mmol) is added to a solution, maintained at 0° C. under argon, of 2'-deoxy-2'-(2-(trimethylsilyl)ethyl)thiothymidine 46 (2.51 g, 6.68 mmol) in anhydrous pyridine (15 ml). After 24 hours, the solvent is evaporated and coevaporated with toluene. The residue is taken up in dichloromethane and the solution is washed with water (100 ml) and dried over magnesium sulfate. After evaporating to dryness, the product is chromatographed on silica gel in a dichloromethane-methanol (98:2) mixture with 2% of triethylamine and exists in the form of a white solid (3.46 g, 5.11 mmol, 76%).

Triethylamine (2.14 ml, 1.53 mmol) and then mesyl chloride (0.88 g, 7.71 mmol) are added to this protected compound, dissolved beforehand in 25 ml of dichloromethane. After 15 h at ambient temperature, 5 ml of water are added and the solvents are evaporated. The residue obtained is taken up in dichloromethane (100 ml), washed with water (50 ml) and dried over magnesium sulfate before being evaporated to dryness. The residue obtained (2.71 g, 4 mmol) is treated with 30 ml of 2% dichloroacetic acid in dichloromethane. This solution is left stirring and under argon for 30 min, before being neutralized with a sodium bicarbonate solution (5%, 80 ml). The aqueous phase is extracted with dichloromethane (100 ml) and the organic phases are dried over sodium sulfate before being evaporated to dryness. The residue is purified on silica gel with a dichloromethane-methanol (98:2) mixture in order to result in the product 14 (1.21 g, 2.67 mmol, 45% for the 2 stages). This compound (297 mg, 0.66 mmol) is dissolved in 15 ml of acetonitrile and potassium carbonate (525 mg, 3.8 mmol) is added. After 3 days at 90° C., the solvents are evaporated and the product 14, after purification on silica gel in a dichloromethane-methanol (98:2) mixture, exists in the form of a white solid (198 mg, 55 mmol, 84%). The overall reaction yield for the 4 stages is 28%.

M.p.: 69° C.

$^1$H NMR (400 MHz, CDCl$_3$) δ 8.73 (1 H, s, NH), 7.38 (1 H, s, 6-H), 6.94 (1 H, m, 1'-H), 5.81 (1 H, s, 3'-H), 4.98 (1 H, s, 4'-H), 3.97-3.74 (2 H, m, 5'-H), 2.85 (2 H, m, S—CH$_2$), 1.87 (3 H, s, 5-CH$_3$), 0.94 (2 H, m, CH$_2$—Si), 0.07 (9 H, s, Si(CH$_3$)$_3$).

$^{13}$C NMR (100 MHz, DMSO) δ 164.0 (C2), 150.6 (C4), 136.9 (C6), 135.2 (C2'), 123.5 (C3'), 110.9 (C5), 90.3 (C1'), 87.4 (C4'), 63.5 (5'-CH$_2$), 28.5 (S—CH$_2$), 16.3 (CH$_2$—Si), 12.4 (CH$_3$), −1.8 (Si(CH$_3$)$_3$).

MS (DCI, NH$_3$-isobutane) m/z 357 [M+H]$^+$.

2',3'-Didehydro-2',3'-dideoxy-2'-(2-(trimethylsilyl)ethyl)thiouridine 18

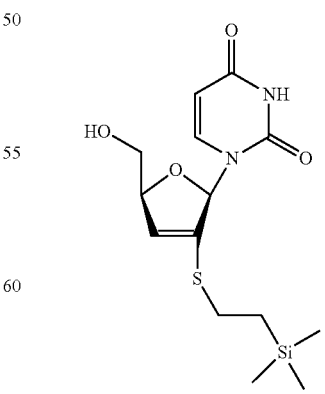

The compound 47 (3.716 g, 7.24 mmol) is dissolved in 50 ml of acetonitrile and potassium carbonate (6.04 g, 43.44 mmol) is added. After 3 days at 90° C., the solvent is evaporated and the product 18, after purification on silica gel in a dichloromethane-methanol (98:2) mixture, exists in the form of a white solid 18 (2.55 g, 7.44 mmo), 85%).

$^1$H NMR (400 MHz, CDCl$_3$) δ 9.30 (1 H, s, NH), 7.61 (1 H, d, J=8 Hz, 6-H), 6.94 (1 H, m, 1'-H), 5.81 (1 H, s, 3'-H), 5.70 (1 H, d, J=8 Hz, 5-H), 4.99 (1 H, m, 4'-H), 3.94-3.74 (2 H, m, 5'-H×2), 2.85 (2 H, m, S—CH$_2$), 0.94 (2 H, m, CH$_2$—Si), 0.09 (9 H, s, Si(CH$_3$)$_3$).

$^{13}$C NMR (100 MHz, CDCl$_3$) δ 164.1 (C2), 150.8 (C4), 141.3 (C6), 134.9 (C2'), 123.6 (C3'), 102.5 (C5), 90.2 (C1'), 87.5 (C4'), 63.4 (5'-CH$_2$), 28.4 (S—CH$_2$), 16.2 (CH$_2$—Si), −1.9 (Si(CH$_3$)$_3$).

MS (DCI, NH$_3$-isobutane) m/z 343 [M+H]$^+$.

Microanalysis for C$_{14}$H$_{22}$N$_2$O$_4$SSi.0.5H$_2$O:

Calculated C, 47.84; H, 6.60; N, 7.97; S, 9.12.

Found C, 47.92; H, 6.76; N, 7.96; S, 9.86.

2',3'-Didehydro-2',3'-dideoxy-2'-(2-(trimethylsilyl)ethyl)thiocytidine 19

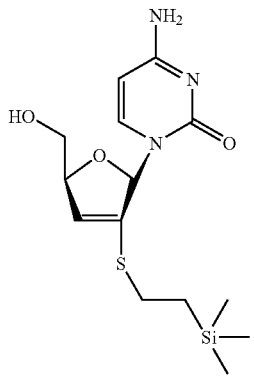

Ammonium fluoride in solution in methanol (813 μl, 0.5M, 0.41 mmol) is added to 50 (0.150 g, 0.31 mmol). The solution is brought to reflux for 6 hours and is then left to return to ambient temperature overnight. The solvents are evaporated and then a dry deposit layer is produced on silica gel in order to chromatograph the final product on silica gel with a dichloromethane-methanol (90:10) mixture. The derivative 19 (0.81 g, 0.24 mmol, 76%) is thus obtained in the form of a white foam.

M.p.: 91-115° C. (decomposition)

$^1$H NMR (400 MHz, MeOD) δ 7.86 (1 H, d, J=7.6 Hz, 6-H), 6.99 (1 H, m, 1'-H), 5.94 (1 H, bs, 3'-H), 5.89 (1 H, d, J=7.6 Hz, 5-H), 4.90 (1 H, m, 4'-H), 3.73 (2 H, m, 5'-H×2), 2.89 (2 H, m, S—CH$_2$), 0.95 (2 H, m, CH$_2$—Si), 0.07 (9 H, s, Si (CH$_3$)$_3$).

$^{13}$C NMR (100 MHz, MeOD), δ 166.2 (C4), 157.3 (C2), 142.1 (C6), 135.4 (C2'), 123.9 (C3'), 95.1 (C5), 90.6 (C1'), 87.4 (C4'), 62.8 (5'-CH$_2$), 27.6 (S—CH$_2$), 15.9 (CH$_2$—Si), −3.3 (Si(CH$_3$)$_3$).

MS (DCI, NH$_3$-isobutane) m/z 342 [M+H]$^+$.

Microanalysis for C$_{30}$H$_{43}$N$_3$O$_4$SSi.0.7H$_2$O:

Calculated C, 48.55; H, 7.13; N, 11.58; S, 8.84.

Found C, 48.26; H, 7.15; N, 11.59; S, 9.08.

3'-Deoxy-3'-(2-(trimethylsilyl)ethyl)thiothymidine sulfoxide 28

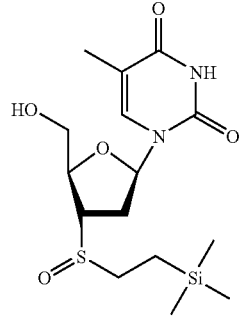

A solution of sodium periodate (0.06 g, 0.28 mmol) in water (700 μl) is added at 0° C. to a solution of 1 (0.1 g, 0.28 mmol) in methanol (1.4 ml). The reaction mixture is allowed to return to ambient temperature overnight. The precipitate is filtered off through a cotton wool pad and then the filtrate is evaporated under vacuum. The residue obtained is flash chromatographed on silica gel in a dichloromethane-methanol (95:5) mixture to give the two inseparable diastereoisomers 28 (0.104 g, 0.16 mmol, quantitative) in the form of a white powder.

Ratio 43 A/57 B $^1$H NMR (400 MHz, CDCl$_3$) δ 9.80 (2 H, bs, 2×NH), 7.57 (1H, s, 6-HA), 7.40 (1H, s, 6-HB), 5.98 (1 H, m, 1'-HA), 5.87 (1 H, dd, J=7.5 Hz, J=4.6 Hz, 1'-HB), 4.60 (1 H, m, 4'-HA), 4.32 (1 H, m, 4'-HB), 4.08-4.05 (2 H, m, 5'-HA, 5'-HB), 3.86-3.80 (2 H, m, 5'-HA, 5'-HB), 3.70 (2 H, m, 3'-HA, 3'-HB), 3.06 (1 H, m, 2'-HB), 2.76-2.50 (4 H, m, S—CH$_2$), 2.48-2.44 (3 H, m, 2'-H×2 A, 2'-HB), 1.89 (6 H, bs, 5-CH$_3$ A, 5-CH$_3$ B), 1.04 (2 H, m, CH—SiA, CH—SiB), 0.83 (2 H, m, CH—Si A, CH—Si B), 0830.06 (9 H, s, Si(CH$_3$)$_3$).

$^{13}$C NMR (100 MHz, CDCl$_3$) δ 164.1 (C2A, B), 150.5 (C4 A, B), 138.0 (C6'B), 136.8 (C6'A), 110.8 (C5 A, B), 88.9 (C1' B), 87.0 (C1' A), 81.4 (C4' A, B), 63.3 (5'-CH$_2$), 61.5 (5'-CH$_2$), 56.7 (C3'), 55.6 (C3'), 47.0 (S—CH$_2$), 46.9 (S—CH$_2$), 33.8 (C2' A), 27.6 (C2' B), 12.4 (5-CH$_3$ A, B), 9.7 (CH$_2$—Si), 8.8 (CH$_2$—Si), −2.0 (Si (CH$_3$)$_3$×2).

MS (DCI, NH$_3$-isobutane) m/z 375 [M+H]$^+$.

2'-Deoxy-2'-(2-(trimethylsilyl)ethyl)thiouridine sulfoxide 32

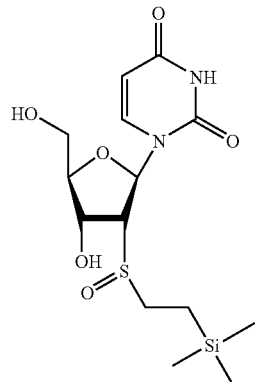

A solution of sodium periodate (119 mg, 0.55 mmol) in water (2.8 ml) is added at 0° C. to a solution of 2'-deoxy-2'-(2-(trimethylsilyl)ethyl)thiouridine 5 (0.2 g, 0.55 mmol) in methanol (5.5 ml). The reaction mixture is allowed to return to ambient temperature overnight. The precipitate is filtered through a cotton wool pad and then the filtrate is evaporated under vacuum. The residue obtained is flash chromatographed on silica gel in a dichloromethane-methanol (90:10 and then 80:20) mixture. The two diastereoisomers 32a and 32b are obtained in the form of a white powder (1:0.080 g; 0.21 mmol; 2:0.065 g; 0.17 mmol; 55/45; 70%).

Diastereoisomer 32a (S Configuration)

$^1$H NMR (400 MHz, CD$_3$OD) δ 8.15 (1 H, d, J=8.0 Hz, 6-H), 6.48 (1 H, d, J=8.0 Hz, 1'-H), 5.81 (1 H, d, J=8.0 Hz, 5-H), 4.74 (1 H, m, 4'-H), 4.13 (1 H, m, 3'-H), 3.86 (1 H, m, J=8.4 Hz, J=5.6 Hz, 2'-H), 3.79 (2 H, m, 5'-H×2), 2.98 (2 H, m, S—CH$_2$), 0.88 (2 H, m, CH$_2$Si), −0.05 (9 H, s, Si(CH$_3$)$_3$).

$^{13}$C NMR (100 MHz, CD$_3$OD) δ 164.1 (C2), 150.8 (C4), 140.9 (C6), 102.7 (C5), 87.7 (C3'), 82.7 (C1'), 72.7 (C4'), 66.9 (C2'), 61.5 (5'-CH$_2$), 44.6 (S—CH$_2$), 7.7 (CH$_2$—Si), −3.5 (Si(CH$_3$)$_3$).

MS (DCI, NH$_3$-isobutane) m/z 377 [M+H]$^+$.

Diastereoisomer 32b (R Configuration)

$^1$H NMR (400 MHz, CD$_3$OD) δ 7.91 (1 H, d, J=8.0 Hz, 6-H), 6.69 (1 H, d, J=8.0 Hz, 1'-H), 5.81 (1 H, d, J=8.2 Hz, 5-H), 4.74 (1 H, m, 4'-H), 4.13 (1 H, m, 3'-H), 3.77 (1 H, dd, J=8.4 Hz, J=5.6 Hz, 2'-H), 3.79 (2 H, m, 5'-H), 2.75 (2 H, m, S—CH$_2$), 1.04 (1 H, m, CHSi), 0.80 (1 H, m, CHSi), 0.88 (2 H, m, CH$_2$Si), 0.10 (9 H, s, Si(CH$_3$)$_3$).

$^{13}$C NMR (100 MHz, CD$_3$OD) δ 164.5 (C2), 150.2 (C4), 141.5 (C6), 102.0 (C5), 85.7 (C4'), 83.5 (C1'), 69.7 (C3'), 65.6 (C2'), 60.1 (5'-CH$_2$), 45.4 (S—CH$_2$), 8.7 (CH$_2$—Si), −3.4 (Si(CH$_3$)$_3$).

MS (DCI, NH$_3$-isobutane) m/z 377 [M+H]$^+$.

2',3'-Dideoxy-3'-(2-(trimethylsilyl)ethyl)thiouridine

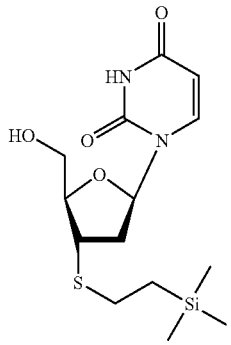

A solution of 2-(trimethylsilyl)ethanethiol (980 µl, 7.02 mmol) in DMF (8 ml) is added to a suspension of a sodium hydride (60%, 234 mg, 7.02 mmol) in anhydrous DMF (8 ml). This mixture is left stirring and under argon for 15 min and then the derivative 51 (3 g, 5.85 mmol) is added. After 24 h under argon at 90° C., the unreacted sodium hydride is neutralized with 3 ml of methanol and the solvents are evaporated under reduced pressure. The residue is subsequently taken up in dichloromethane (100 ml) and the solution is neutralized with a NaH$_2$PO$_4$ solution (10%, 10 ml), washed with water (100 ml) and dried over sodium sulfate before being evaporated to dryness. The residue is taken up in dichloromethane in order to be chromatographed on silica gel with a dichloromethane-ethyl acetate (8:2) mixture comprising 1% of triethylamine and to give the sulfide in the form of a yellow foam.

The pale yellow foam obtained is dissolved in a solution of dichloroacetic acid in dichloromethane (2%, 80 ml). The orange solution obtained is left stirring and under argon for 4 hours before being neutralized with a sodium bicarbonate solution (5%, 30 ml). The aqueous phase extracted with dichloromethane (50 ml) and the organic phases are combined in order to be dried over sodium sulfate before being evaporated to dryness. The residue is taken up in dichloromethane in order to be chromatographed on silica gel with a dichloromethane-ethyl acetate (6:4) mixture and to give the sulfide 35 (1.06 g, 3.08 mmol, 56% (2 stages)) in the form of a white solid.

M.p.: 148° C.

$^1$H NMR (400 MHz, CDCl$_3$) δ 9.47 (1 H, s, NH), 7.82 (1H, d, J=8.4 Hz, 6-H), 6.12 (1 H, dd, J=7.0 Hz, J=3.6 Hz, 1'-H), 5.73 (1 H, d, J=8.4 Hz, 5-H), 4.05 (1 H, m, 3'-H), 3.85 (2 H, m, 5'-H×2), 3.47 (1 H, m, 4'-H), 2.64-2.50 (4 H, m, 2'-H×2, S—CH$_2$), 0.84 (2 H, m, CH$_2$—Si), −0.02 (9 H, s, Si(CH$_3$)$_3$).

$^{13}$C NMR (100 MHz, CDCl$_3$) δ 163.9 (CO), 150.4 (CO), 140.9, 101.9, 86.2, 85.7, 61.0 (5'-CH$_2$), 40.7, 40.1 (2'-CH$_2$), 27.5 (S—CH$_2$), 17.4 (CH$_2$—Si), −1.8 (Si (CH$_3$)$_3$).

MS (FAB+, glycerol) m/z=345 [M+H]$^+$.

Microanalysis for C$_{14}$H$_{24}$N$_2$O$_4$SSi.0.33H$_2$O:

Calculated C, 47.97; H, 7.09; N, 7.99; S, 9.15.

Found C, 47.82; H, 7.13; N, 7.79; S, 9.66.

2'-Deoxy-2'-(2-(trimethylsilyl)ethyl)thiothymidine 46

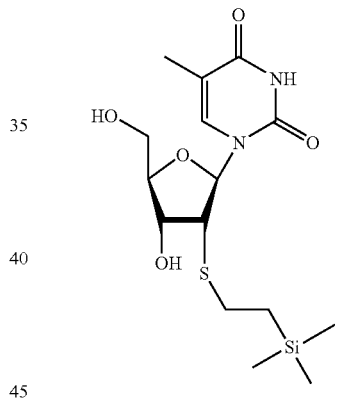

2-(trimethylsilyl)ethanethiol (3.5 g, 26 mmol) is added to a suspension of 2,2'-anhydrothymidine (5 g, 22 mmol) and anhydrous potassium carbonate (11 g, 79 mmol) in DMF (110 ml). The solution is left stirring and under argon at 120° C. for 3 h. After filtering off and rinsing the inorganic salts with dichloromethane, the solvents are evaporated under reduced pressure to give a yellow oil. This residue is chromatographed on silica gel in a dichloromethane-methanol (95:5) mixture. The sulfide 46 is obtained in the form of a white solid (6.9 g, 19 mmol, 88%).

M.p.: 58-60° C.

$^1$H NMR (400 MHz, CDCl$_3$) δ 8.73 (1H, s, NH), 7.25 (1 H, d, J=8.0 Hz, 6-H), 5.46 (1 H, d, J=9.2 Hz, 1'-H), 4.36 (1 H, m, 3'-H), 4.24 (1 H, m, 4'-H), 3.99 (2 H, m, 2'H+5'-H), 3.81 (1 H, m, 5'-H), 2.60 (2 H, m, S—CH$_2$), 1.96 (3 H, s, 5-CH$_3$), 0.85 (2 H, m, CH$_2$Si), −0.02 (9 H, s, Si(CH$_3$)$_3$).

$^{13}$C NMR (100 MHz, CDCl$_3$) δ 163.4 (C2), 150.5 (C4), 138.87 (C6), 111.4 (C5), 93.3 (C1'), 86.6 (C4'), 71.5 (C3'), 63.1 (5'-CH$_2$), 52.8 (C2'), 28.4 (S—CH$_2$), 18.1 (CH$_2$—Si), 12.4 (CH$_3$), −1.8 (Si (CH$_3$)$_3$)

MS (DCI, NH$_3$-isobutane) m/z 375 [M+H]$^+$, 392 [M+H+NH$_3$]$^+$.

2'-Deoxy-3'-(O-mesyl)-2'-(2-(trimethylsilyl)ethyl) thiouridine 47

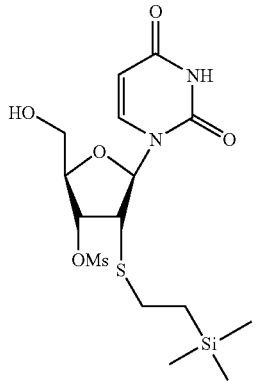

4,4'-dimethoxytrityl chloride (5.20 g, 15.3 mmol) is added to a solution, maintained at 0° C. under argon, of 2'-deoxy-2'-(2-(trimethylsilyl)ethyl)thiouridine 5 (3 g, 13.8 mmol), compound of formula (IIa), in anhydrous pyridine (50 ml). After 24 hours, the solvent is evaporated and coevaporated with toluene. The residue is taken up in dichloromethane and the solution is washed with water (100 ml) and dried over magnesium sulfate. After evaporating to dryness, the product is purified on silica gel in a dichloromethane-methanol (98:2) mixture comprising 2% of triethylamine and exists in the form of a white solid (7.23 g, 10.91 mmol, 91%).

Mesyl chloride (1 ml, 12.85 mmol) is added to this tritylated compound (7.1 g, 10.71 mmol) dissolved beforehand in 50 ml of anhydrous pyridine. The solution is maintained under argon and at 0° C. for 1 hour and is then allowed to return to ambient temperature for 15 h. 5 ml of water are subsequently added and the solvents are evaporated. The residue obtained is taken up in dichloromethane (100 ml) and the solution is washed with water (50 ml) and dried over magnesium sulfate before being evaporated to dryness.

The residue obtained (8.36 g, 11.28 mmol), dissolved in 20 ml of dichloromethane, is treated with 80 ml of 2% dichloroacetic acid in dichloromethane. This solution is left stirring for 4 hours, before being neutralized with a sodium bicarbonate solution (5%, 80 ml). The aqueous phase is extracted twice with dichloromethane (100 ml) and the combined organic phases are dried over magnesium sulfate before being evaporated to dryness. The residue is purified on silica gel with a dichloromethane-methanol (98:2) mixture to result in the product 47 (3.716 g, 7.24 mmol, i.e. 71% for the 3 stages).

$^1$H NMR (400 MHz, CDCl$_3$) δ 7.50 (1 H, d, J=8.0 Hz, 6-H), 5.83 (1 H, d, J=8.1 Hz, 5-H), 5.70 (1 H, d, J=9.3 Hz, 1'-H), 5.31 (1 H, m, 3'-H), 4.47 (1 H, bs, 4'-H), 4.04 (1 H, dd, J=9.3 Hz, J=5.5 Hz, 2'-H), 3.93 (2 H, m, 5'-H×2), 3.18 (3 H, s, CH$_3$), 2.58 (2 H, m, S—CH$_2$), 0.80 (2 H, m, CH$_2$Si), 0.01 (9 H, s, Si(CH$_3$)$_3$).

$^{13}$C NMR (100 MHz, CDCl$_3$) δ 162.4 (C2), 150.3 (C4), 142.5 (C6), 103.2 (C5), 93.9 (C1'), 85.5 (C4'), 81.9 (C3'), 62.2 (5'-CH$_2$), 48.7 (C2'); 38.5 (CH$_3$, Ms), 28.2 (S—CH$_2$), 17.8 (CH$_2$—Si), −1.9 (Si(CH$_3$)$_3$).

MS (DCI, NH$_3$-isobutane m/z 439 [M+H]$^+$, 456 [M+H+Na]$^+$.

5'-O-(tert-Butyldiphenylsilyl)-2'-(2-(trimethylsilyl) ethyl)thiocytidine 48

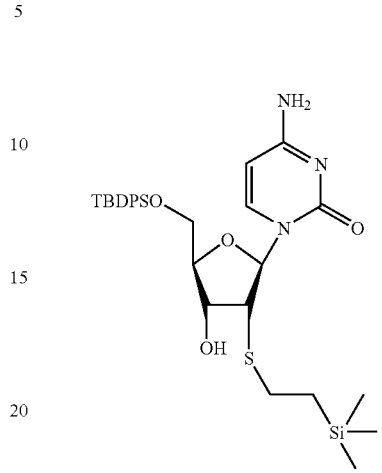

The compound 6 (1 g, 2.78 mmol) is dissolved in anhydrous pyridine (15 ml) at 0° C. under argon. After 15 minutes, tert-butyldiphenylsilyl chloride (870 μl, 3.34 mmol) is added and the mixture is left stirring for 48 h. After evaporation and coevaporation with toluene, the residue obtained is dissolved in dichloromethane (100 ml) and then washed with water (50 ml). The organic phase is subsequently dried over magnesium sulfate and evaporated and coevaporated with toluene (100 ml). The solid obtained is chromatographed on silica gel in a dichloromethane-methanol (95:5) mixture and gives the compound 48 (1.37 g, 2.29 mmol, 83%) in the form of a white powder.

M.p.: 126° C.

$^1$H NMR (400 MHz, CDCl$_3$) δ 7.89 (1 H, d, J=7.2 Hz, 6-H), 7.69-7.65 (4 H, m, Ar), 7.51-7.37 (6 H, m, Ar), 6.28 (1 H, d, J=6.8 Hz, 1'-H), 5.50 (1 H, d, J=7.6 Hz, 5-H), 4.41 (1 H, m, 3'-H), 4.08-4.03 (2 H, m, 5'-H×2), 3.85 (1 H, m, 4'-H), 3.47 (1 H, m, 2'-H), 2.65 (2 H, m, S—CH$_2$), 1.16 (9 H, s, tBu), 0.86 (2 H, m, CH$_2$—Si), 0.08 (9 H, s, Si(CH$_3$)$_3$).

$^{13}$C NMR (100 MHz, CDCl$_3$) δ 165.6 (C4), 155.9 (C2), 140.7 (C6), 135.6 (2C, Ar), 135.3 (2C, Ar), 132.7 (1C, Ar), 132.1 (1C, Ar), 130.1 (1C, Ar), 130.01 (1C, Ar), 127.91 (2C, Ar), 127.91 (2C, Ar), 95.1 (C5), 88.2 (C1'), 85.2 (C4'), 70.3 (C3'), 63.8 (5'-CH$_2$), 56.0 (C2'), 28.2 (S—CH$_2$), 26.9 ((CH$_3$)$_3$), 18.4 (C(CH$_3$)$_3$), 17.8 (CH$_2$—Si), −1.8 (Si(CH$_3$)$_3$)

MS (FAB+, NAB+NaCl) m/z 598 [M+H]$^+$, 620 [M+Na]$^+$, 112 [cytosine+H]$^+$.

Microanalysis for C$_{30}$H$_{43}$N$_3$O$_4$SSi:

Calculated C, 60.26; H, 7.25; N, 7.03; S, 5.36.

Found C, 60.03; H, 7.38; N, 6.82; S, 5.32.

N-4-Benzoyl-3'-(O-mesyl)-5'-(O-tert-butyl-diphenyl-silyl)-2'-(2-(trimethylsilyl)ethyl)thiocytidine

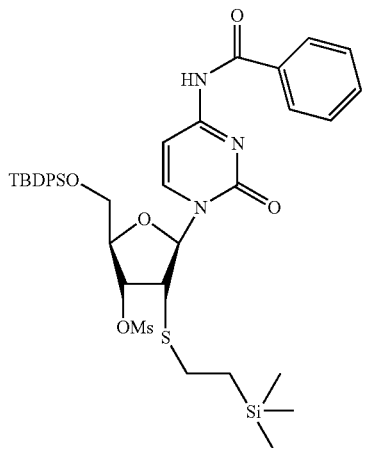

Benzoic anhydride (497 mg, 2.2 mmol) is added to a solution of 48 (1.3 g, 2.2 mmol) in anhydrous DMF (15 ml). The mixture is brought to reflux for 24 hours and then 0.2 equivalent of anhydride is again added. The next day, the solvent is evaporated and then the residue is dissolved in dichloromethane in order to be extracted twice with water.

Mesyl chloride (194 μl, 2.5 mmol) is added to the crude residue in pyridine (15 ml) at 0° C. under argon. The mixture is kept stirred for 15 h and then neutralized by addition of water (15 ml) at 0° C. After 30 minutes, the solvents are evaporated and the residue is coevaporated with toluene. It is subsequently dissolved in dichloromethane in order to be washed with water (50 ml) and dried over magnesium sulfate before being evaporated to dryness. The foam obtained is chromatographed on silica gel with a dichloromethane-methanol (98:2) mixture to give the white solid 49 (1.57 g, 2.01 mmol, 91% for the two stages).

$^1$H NMR (400 MHz, CDCl$_3$) δ 8.71 (1 H, bs, NH), 8.41 (1 H, d, J=7.4 Hz, 6-H), 7.69-7.28 (15 H, m, Ar), 7.68 (5 H, m, Ar—H), 7.56-7.43 (10 H, m, Ar—H), 7.27 (1 H, d, J=7.6 Hz, 5-H), 6.43 (1 H, d, J=7.6 Hz, 1'-H), 5.34 (1 H, m, 3'-H), 4.43 (1 H, m, 4'H), 4.09-3.95 (2 H, m, J=1.9 Hz, J=12.0 Hz, 5'-H×2), 3.64 (1 H, m, 2'-H), 3.15 (3 H, s, CH$_3$, Ms), 2.65 (2 H, m, S—CH$_2$), 1.16 (9 H, s, tBu), 0.80 (2 H, m, Si—CH$_2$), 0.04 (9 H, s, Si (CH$_3$)$_3$).

$^{13}$C NMR (100 MHz, CDCl$_3$) δ 169.5 (CO), 162.3 (C4), 150.1 (C2), 144.1 (C6), [135.6, 135.3, 133.2, 132.2, 131.58, 130.4, 130.3, 129.0, 128.3, 128.2, 127.6] (Ar), 97.9 (C5), 89.2 (C1'), 84.2 (C4'), 79.3 (C3'), 62.9 (5'-CH$_2$), 52.0 (C2'), 38.7 (CH$_3$ Ms), 27.8 (S—CH$_2$), 27.1 ((CH$_3$)$_3$), 17.5 (C(CH$_3$)$_3$), 17.5 (CH$_2$—Si), −1.9 (Si(CH$_3$)$_3$).

MS (FAB+, NAB+NaCl) m/z 780 [M+H]$^+$, 802 [M+Na]$^+$.
Microanalysis for C$_{38}$H$_{49}$N$_3$O$_7$S$_2$Si$_2$:
Calculated C, 58.51; H, 6.33; N, 5.39; S, 8.22.
Found C, 58.26; H, 6.45; N, 5.32; S, 8.45.

2',3'-Didehydro-2',3'-dideoxy-5'-(O-tert-butyldiphenylsilyl)-2'-(2-(trimethylsilyl)ethyl)thiocytidine 50

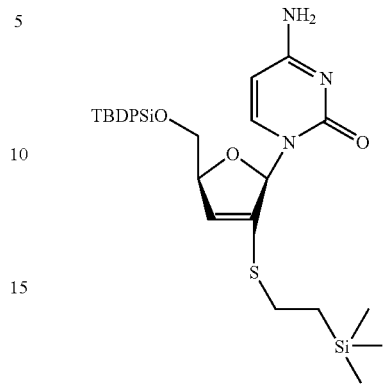

Aqueous ammonia (10 ml) is added to a solution of 49 (1.4 g, 1.79 mmol) in ethanol. The solution is kept stirred at ambient temperature for 24 hours. The solvent is subsequently evaporated and the residue is chromatographed on silica gel with a dichloromethane-methanol (95:5) mixture to give a white solid (1.15 g, 1.71 mmol, 95%).

Potassium carbonate (1.24 g, 8.82 mmol) is added to the product (1 g, 1.47 mmol) dissolved in acetonitrile (10 ml) and then the reaction mixture is maintained at ambient temperature and under argon for 48 h. The inorganic salts are removed by filtration through celite and the solvents are evaporated. The product is taken up in dichloromethane in order to be chromatographed on silica gel with a dichloromethane-methanol (95:5) mixture. The derivative 50 (0.510 g, 1.06 mmol, 72%) is thus obtained in the form of a white foam.

M.p.: 122-123° C.

$^1$H NMR (400 MHz, CDCl$_3$) δ 7.66 (4, m, Ar), 7.57 (1 H, d, J=7.6 Hz, 6-H), 7.42 (6 H, m, Ar), 7.12 (1 H, m, 1'-H), 5.74 (1 H, m, 3'-H), 5.28 (1 H, d, J=7.6 Hz, 5-H), 4.92 (1 H, m, 4'-H), 4.08-4.03 (2 H, m, J=3.2 Hz, J=12.0 Hz, 5'-H×2), 2.82 (2 H, m, S—CH$_2$), 1.09 (9 H, 2, tBu), 0.96 (2 H, m, CH$_2$—Si), 1.01 (9 H, s, Si(CH$_3$)$_3$).

$^{13}$C NMR (100 MHz, CDCl$_3$) δ 165.5 (C4), 156.2 (C2), 141.9 (C6), 136.5 (Ar), 135.5 (C2'), 133.4 (Ar), 129.9 (Ar), 127.8 (Ar), 122.9 (C3'), 127.91 (2CAr), 95.1 (C5), 90.4 (C1'), 86.5 (C4'), 65.7 (5'-CH$_2$), 28.2 (S—CH$_2$), 26.9 ((CH$_3$)$_3$), 19.3 (C(CH$_3$)$_3$), 16.4 (CH$_2$—Si), −1.8 (Si(CH$_3$)$_3$).

MS (FAB+, NAB+NaCl) m/z 580 [M+H]$^+$, 602 [M+Na]$^+$.
Microanalysis for C$_{30}$H$_{43}$N$_3$O$_4$SSi.0.5MeOH:
Calculated C, 61.47; H, 7.27; N, 7.05; S, 5.38.
Found C, 61.49; H, 7.36; N, 7.05; S, 5.75.

2,3'-Anhydro-2'-deoxy-5'-O-(4,4'-dimethoxytrityl) uridine 51

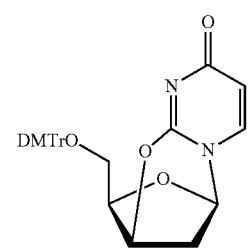

4,4'-Dimethoxytrityl chloride (5.39 g, 15.9 mmol) is added to a solution, maintained under argon at 0° C., of 2'-deoxyuridine (3.3 g, 14.5 mmol) in anhydrous pyridine (50 ml). The mixture is left stirring for 1 hour at 0° C. and then for 24 h at ambient temperature. Mesyl chloride (1.35 ml, 17.4 mmol) is added and the mixture is left reacting for 4 hours. Water (5 ml) is subsequently added and, after 30 minutes, the solvents are evaporated and coevaporated with toluene. The residue obtained is taken up in dichloromethane (100 ml) and the solution is washed with water (50 ml) and dried over sodium sulfate before being evaporated to dryness. The yellow foam obtained is dissolved in the minimum amount of dichloromethane in order to be chromatographed on silica gel in a dichloromethane-methanol (95:5) mixture comprising 1% of triethylamine.

The white foam obtained is dissolved in anhydrous acetonitrile (60 ml) and potassium carbonate (6 g, 43.1 mmol) is added. The mixture is left stirring and under argon for 48 h at ambient temperature and then for 2 hours at reflux before being filtered. The filtrate is subsequently evaporated to dryness and the residue obtained is taken up in dichloromethane (100 ml) to be washed with water (80 ml) and dried over sodium sulfate. After evaporation, the solid obtained is chromatographed on silica gel in a dichloromethane-methanol (95:5) mixture comprising 1% of triethylamine to give the tritylated compound 51 (5.79 g, 11.3 mmol, 78%) in the form of a white powder.

M.p.: 255° C.
$^1$H NMR (400 MHz, CDCl$_3$) δ 7.42-7.07 (10 H, m, Ar—H), 6.84-6.08 (3 H, m, Ar—H), 5.90 (1 H, d, J=7.36 Hz, 6-H), 5.52 (1 H, d, J=4.01 Hz, 5-H), 5.15 (1 H, m, 1'-H), 4.26 (1 H, m, 3'-H), 3.79 (6 H, s, 2×O—CH$_3$), 3.40-3.31 (2 H, m, 5'-H×2), 2.61 (1 H, m, 4'-H), 2.38 (2 H, m, 2'H×2).
$^{13}$C NMR (100 MHz, CDCl$_3$) δ 171.0, 158.5, 153.5, 144.4, 139.1, 135.3, 135.3, 129.9, 127.9, 127.8, 126.8, 113.2, 109.5, 87.6, 86.7, 84.5, 61.9, 55.2 (O—CH$_3$), 32.7 (2'-CH$_2$)—
MS (FAB+, glycerol) m/z 513 [M+H]$^+$.
Microanalysis for C$_{30}$H$_{28}$N$_2$O$_6$.0.5H$_2$O:
Calculated C, 69.09; H, 5.60; N, 5.37.
Found C, 68.99; H, 5.57; N, 5.37.

1-(3'-(2-(trimethylsilyl)ethylthio)-β-D-xylofuranos-1'-yl)thymine 52

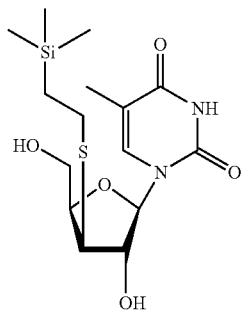

Sodium hydride (65%, 1.10 g, 29.9 mmol) is added at 0° C. to a suspension of 2,2'-anhydrothymidine (0.6 g, 2.49 mmol) in anhydrous DMF (15 ml) followed, after 3 h at ambient temperature under argon and with stirring, by 2-(trimethylsilyl)ethanethiol (0.75 ml, 3.96 mmol). The solution is left stirring under argon at ambient temperature for 3 h. The reaction mixture is subsequently placed at 0° C. and an aqueous ammonium chloride solution (10%, 10 ml) is added. The solvents are evaporated under reduced pressure and the residue obtained is taken up in dichloromethane (100 ml) in order to be washed twice with water (50 ml). The organic phases are combined and dried over magnesium sulfate before being evaporated to dryness. The yellow residue obtained is chromatographed on silica gel in a dichloromethane-methanol (95:5) mixture. The sulfide 52 is obtained in a form of a white solid (0.734 g, 1.96 mmol, 79%).

$^1$H NMR (400 MHz, CDCl$_3$) δ 10.34 (1 H, s, NH), 7.66 (1 H, s, 6-H), 5.68 (1 H, bd, J=4.2 Hz, 1'-H), 5.78 (1 H, d, J=8.0 Hz, 5-H), 4.55 (1 H, m, 4'-H), 4.38 (1 H, m, 2'-H), 3.91-3.87 (2 H, m, 5'-H), 2.67 (2 H, m, S—CH$_2$), 0.85 (2 H, m, CH$_2$Si), −0.01 (9 H, s, Si(CH$_3$)$_3$).
$^{13}$C NMR (100 MHz, CDCl$_3$) δ 164.3 (C2), 151.3 (C4), 136.5 (C6), 110.4 (C5), 91.2 (C1'), 80.6 (C4'), 80.9 (C2'), 62.8 (5'-CH$_2$), 50.5 (C3'), 28.6 (S—CH$_2$), 16.2 (CH$_2$—Si), −1.8 (Si(CH$_3$)$_3$).
MS (DCI, NH$_3$/isobutane) m/z 375 [M+H]$^+$.

2,2'-Anhydro-5'-(O-benzoyl)-1-(3'-(2-(trimethylsilyl)ethylthio)-β-D-xylofuranos-1'-yl)thymine 53

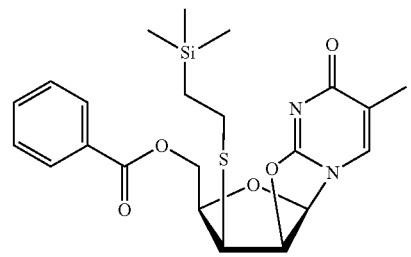

Diisoethyl azodicarboxylate (DEAD) (87 μl, 0.56 mmol) is added to a mixture of 52 (0.135 g, 0.36 mmol), triphenylphosphine (0.144 g, 0.56 mmol) and benzoic acid (0.068 g, 0.56 mmol) in anhydrous THF (3 ml). The mixture is left stirring and at ambient temperature for one and a half hours and then triphenylphosphine (0.144 g, 0.56 mmol) and DEAD (87 μl, 0.56 mmol) are added. After three hours, the solvent is evaporated and then the residue obtained is chromatographed on silica gel in a dichloromethane-methanol (98:2) mixture. The sulfide 53 is obtained in the crude form of a white solid (0.100 g).

$^1$H NMR (400 MHz, CDCl$_3$) δ 7.51 (5 H, m, Ar), 7.19 (1 H, s, 6-H), 6.21 (1 H, d, J=5.6 Hz, 1'-H), 5.29 (1 H, t, J=5.6 Hz, J=11.6 Hz, 2'-H), 4.83 (1 H, m, 4'-H), 4.64 (1 H, dd, J=4.4 Hz, J=12.4 Hz, 5'-H), 4.01 (1H, dd, J=3.2 Hz, J=12.4 Hz, 5'-H), 3.73 (1 H, m, 3'-H), 2.75 (2 H, m, S—CH$_2$), 0.92 (2 H, m, CH$_2$Si), 0.03 (9 H, s, Si(CH$_3$)$_3$).
$^{13}$C NMR (100 MHz, CDCl$_3$) δ 172.2 (CO), 165.7 (C2), 159.4 (C4), 136.8 (C6), 132.1 (Ar), 130.4 (Ar), 129.6 (2 C Ar), 128.5 (2 C Ar), 119.1 (C5), 90.0 (C1'), 83.7 (C4'), 80.2 (C2'), 64.2 (5'-CH$_2$), 48.3 (C3'), 29.0 (S—CH$_2$), 17.6 (CH$_2$—Si), 13.9 (CH$_3$), −1.9 (Si(CH$_3$)$_3$).

2',3'-Didehydro-2',3'-dideoxy-3'-(2-(trimethylsilyl)ethyl)thiothymidine 54

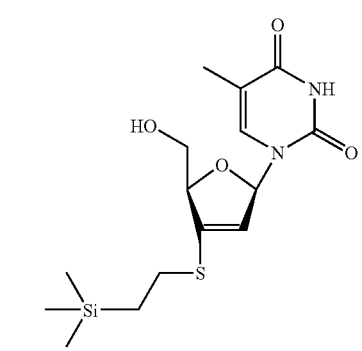

Potassium carbonate (0.2 g, 1.44 mmol) is added to a solution of the compound 53 (0.1 g, 0.22 mmol) in anhydrous acetonitrile. The reaction mixture is kept stirred under argon for 15 hours. The inorganic salts are then removed by filtration through celite and the solvent is evaporated. The product is taken up in methanol and then an aqueous ammonia solution (2 ml) is added. The mixture is left to react for 4 hours and then the solvents are evaporated. The residue is chromatographed on silica gel in a dichloromethane-methanol (98:2 then 95:5) mixture. The unsaturated compound 54 is obtained in the form of a white solid (0.02 g, 0.056 mmol, 16%).

$^1$H NMR (400 MHz, CDCl$_3$) δ 8.60 (1 H, s, NH), 7.64 (1H, s, 6-H), 7.07 (1 H, m, 1'-H), 5.3 (1 H, s, 2'-H), 4.79 (1 H, s, 4'-H), 3.98-3.78 (2 H, m, 5'-H×2), 2.94 (2 H, m, S—CH$_2$), 1.88 (3 H, s, 5-CH$_3$), 1.02 (2 H, m, CH$_2$—Si), 0.07 (9 H, s, Si(CH$_3$)$_3$).

$^{13}$C NMR (100 MHz, CDCl$_3$) δ 163.9 (C2), 150.6 (C4), 144.4 (C2'), 136.8 (C6), 114.1 (C3'), 110.6 (C5), 89.5 (C1'), 87.7 (C4'), 62.4 (5'-CH$_2$), 28.8 (S—CH$_2$), 15.9 (CH$_2$—Si), 12.3 (CH$_3$), -1.9 (Si(CH$_3$)$_3$).

MS (DCI, NH$_3$-isobutane) m/z 357 [M+H]$^+$, 373 [M+NH$_3$]$^+$.

2',3-Dideoxy-3'-(2-(trimethylsilyl)ethyl)thiocytidine 55

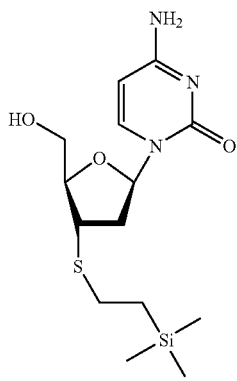

Acetic anhydride (1.23 ml) is added dropwise to a solution of 35 (0.3 g, 0.87 mmol) in anhydrous pyridine (3 ml) at 0° C. The solution is left stirring at ambient temperature and under argon for 24 h. Absolute ethanol (1 ml) is subsequently added at 0° C. After 30 min, the solvents are evaporated, the residue obtained is taken up in dichloromethane (10 ml) and the solution obtained is washed with water (10 ml). The aqueous phase extracted with dichloromethane (15 ml) and the organic phases are subsequently combined, dried over sodium sulfate, evaporated to dryness and coevaporated with toluene (10 ml) to give the acetylated compound in the form of a yellow solid.

1,2,4-Triazole (0.902 g, 13.06 mmol) is added under argon to a solution of POCl$_3$ (292 μl, 2.87 mmol) in anhydrous acetonitrile (5 ml). The solution is left stirring for 15 min at 0° C. and then triethylamine (5 ml, 35.76 mmol) is added dropwise. The mixture obtained is allowed to return to ambient temperature and is kept stirred overnight and then a solution of the acetylated nucleoside obtained above dissolved in acetonitrile (5 ml) is added. The mixture is left stirring at ambient temperature for 48 H, then water (1 ml) is added and the solvents are evaporated. The yellow oil obtained is dissolved in dichloromethane (10 ml) and the solution is neutralized with a sodium bicarbonate solution (10%, 2 ml) and then washed with water (20 ml). The organic phase is subsequently dried over magnesium sulfate, evaporated and coevaporated with toluene (10 ml).

The residue is dissolved in a solution of ammonia in dioxane (50 ml, 0.5M). The solution is left stirring and under argon for 48 h before being evaporated to dryness.

The yellow solid obtained is dissolved in ethanol (10 ml) and a concentrated aqueous ammonia solution (30%, 10 ml) is added. After stirring for 12 H, the solvents are evaporated and coevaporated with ethanol. The residue obtained is chromatographed on silica gel with a dichloromethane-methanol (90:10) mixture. The cytidine derivative 55 (0.25 g, 0.695 mmol, 80%) is thus obtained in the form of a white powder.

$^1$H NMR (400 MHz, MeOD) δ 7.45 (1 H, d, J=7.5 Hz, 6-H), 6.10 (1 H, dd, J=10.0 Hz, J=4.8 Hz, 1'-H), 5.99 (1 H, d, J=7.5 Hz, 5-H), 3.95 (1 H, m, 5'-H), 3.81 (1 H, m, 4'-H), 3.80 (1 H, m, 5'-H), 3.38 (1 H, m, 3'-H), 2.70-2.50 (2 H, m, 2'-H×2), 2.71-2.42 (2 H, m, S—CH$_2$), 0.89 (2 H, m, CH$_2$—Si), 0.05 (9 H, s, Si(CH$_3$)$_3$).

$^{13}$C NMR (100 MHz, MeOD) δ 166.2 (C4), 156.7 (C2), 141.3 (C6), 94.0 (C5), 86.5 (C1'), 85.8 (C4'), 60.3 (5'-CH$_2$), 40.7 (2'-CH$_2$), 39.9 (C4'), 20.6 (S—CH$_2$), 16.9 (CH$_2$—Si), -3.2 (Si(CH$_3$)$_3$).

MS (FAB+, glycerol): m/z=291 [M+H]$^+$.

Microanalysis for C$_{14}$H$_{25}$N$_2$O$_3$S$_2$.0.6H$_2$O:
Calculated C, 47.46; H, 7.45; N, 11.86; S, 9.05.
Found C, 47.65; H, 7.45; N, 11.64; S, 9.28.

The experimental part below describes the influence of the fluoride ions on the preparation of a disulfide according to the invention.

The catalyst (0.2 equivalent) or the 2-nitrobenzene-sulfenyl chloride (32 mg, 0.17 mmol) are or are not added to a solution, maintained under argon, of nucleoside 18 (20 mg, 0.06 mmol) in anhydrous dichloromethane. The mixture is left stirring and is brought to reflux only overnight in order to make sure that the reaction is not complete.

Experiment 1: without catalyst (control)
Experiment 2: in the presence of ammonium fluoride in solution in methanol (22 μl, 0.5M, 0.012 mmol)
Experiment 3: in the presence of ammonium fluoride in solution in methanol (22 μl, 0.5M, 0.012 mmol) but without addition of 2-nitrobenzenesulfenyl chloride
Experiment 4: in the presence of ammonium bromide (1 mg, 0.012 mmol).

The solvent is evaporated and the residue obtained is chromatographed on silica gel in a dichloromethane-methanol (98:2 then 95:5) mixture before determination of the progress of the reaction by integrating the signal of the 3'H proton (in CDCl$_3$) in proton NMR.

For the mixture, ratio of amount of disulfide formed/starting compound:
Experiment 1: 56/44
Experiment 2: 67/33
Experiment 3: 0/100
Experiment 4: 47/53

The silylated starting reactant does not undergo any decomposition: the silylated sulfide unit remains stable in the presence of fluoride ions. On the other hand, the reaction is thus accelerated in the presence of fluoride ions while it is slowed down in the presence of bromide ions.

What is claimed is:

1. A compound of formula (IIa)
R1-S—CH$_2$—CH$_2$—Si(R4)(R5)(R6) as intermediate compound in the preparation of disulfides and thiosulfinates, wherein R1 represents a hydrocarbon molecular residue, which can be substituted and/or interrupted by one or more atoms and/or by one or more groups comprising one or more atoms, said atoms being chosen from the group consisting of N, O, S, Si or X, where X represents a halogen;

R4, R5 and R6, are identical or different, each represent, independently of one another, a hydrocarbon group; and the compound is chosen from the group consisting of:
2'-deoxy-3'-(O-mesyl)-2'-(2-(trimethylsilyl)ethyl)thiouridine 47
5'-O-(tert-butyldiphenylsilyl)-2'-(2-(trimethylsilyl)ethyl)thiocytidine 48
N-4-benzoyl-3'-(O-mesyl)-5'-(O-tert-butyldiphenylsilyl)-2'-(2-(trimethylsilyl)ethyl)thiocytidine 49
1-(3'-(2-(trimethylsilyl)ethylthio)-β-D-xylofuranos-1'-yl)thymine 52 and
2,2'-anhydro-5'-(O-benzoyl)-1-(3'-(2-(trimethylsilyl)ethylthio)-β-D-xylofuranos-1'-yl)thymine 53.

2. A compound of formula (IIa) R1-S—CH$_2$—CH$_2$—Si(R4)(R5)(R6) as intermediate compound in the preparation of disulfides and thiosulfinates, wherein R1 is chosen from 2',3'-didehydro-2',3'-dideoxynucleoside groups, and R4, R5 and R6, which are identical or different, each represent, independently of one another, a hydrocarbon group.

3. The compound as claimed in claim 2, wherein the compound is chosen from the group consisting of:
2',3'-Didehydro-2',3'-dideoxy-2'-(2-(trimethylsilyl)ethyl)thiothymidine 14
2',3'-Didehydro-2',3'-dideoxy-3'-(2-(trimethylsilyl)ethyl)thiothymidine 54
2',3'-Didehydro-2',3'-dideoxy-2'-(2-(trimethylsilyl)ethyl)thiouridine 18
2',3'-Didehydro-2',3'-dideoxy-5'-(O-tert-butyldiphenylsilyl)-2'-(2-(trimethylsilyl)ethyl)thiocytidine 50
2',3'-Didehydro-2',3'-dideoxy-2'-(2-(trimethylsilyl)ethyl)thiocytidine 19.

4. A compound of formula (IIb) R1-SO—R3-Si(R4)(R5)(R6), chosen from the group consisting of:
3'-deoxy-3'-(2-(trimethylsilyl)ethyl)thiothymidine sulfoxide 28
2'-deoxy-2'-(2-(trimethylsilyl)ethyl)thiouridine sulfoxide 32.

5. A compound of formula (III) R1-S—S—R2, wherein R1 represents a 2',3'-dideoxy-2',3'-didehydronucleoside; and R2 represents independently of R1, a carbon group or a hydrocarbon molecular residue, which can be substituted and/ or interrupted by one or more atoms and/ or by one or more groups comprsing one or more atoms, said atoms being chosen from the group consisting of N, O, P, S, Si or X, where X represents a halogen.

6. A compound of formula (III) R1-S—S—R2 chosen from the group consisting of:
3'-Deoxythymidin-3'-yl trichloromethyl disulfide 2
3'-Deoxythymidin-3'-yl 4-nitrophenyl disulfide 3
2'-Deoxyuridin-2'-yl trichloromethyl disulfide 7
2'-Deoxycytidin-2'-yl trichloromethyl disulfide 8
2'-Deoxyuridin-2'-yl 4-nitrophenyl disulfide 9
2'-Deoxycytidin-2'-yl 4-nitrophenyl disulfide 10
3'-Deoxythymidin-3'-yl propyl disulfide 13
2',3'-Didehydro-2',3'-dideoxythymidin-2'-yl trichloromethyl disulfide 15
2',3'-Didehydro-2',3'-dideoxythymidin-2'-yl 4-nitrophenyl disulfide 16
2',3'-Didehydro-2',3'-dideoxythymidin-2'-yl 2-nitrophenyl disulfide 17
2',3'-Didehydro-2',3'-dideoxyuridin-2'-yl trichloromethyl disulfide 20
2',3'-Didehydro-2',3'-dideoxyuridin-2'-yl 4-nitrophenyl disulfide 21 and
2',3'-Didehydro-2',3'-dideoxyuridin-2'-yl and 2-nitrophenyl disulfide 22.

7. A compound of formula (IV) R1-S—SO—R2 consisting of the thiosulfinate 25

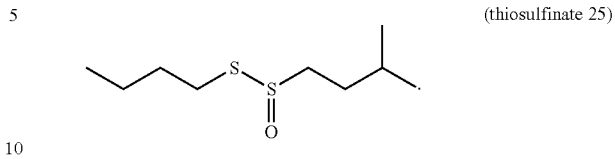

(thiosulfinate 25)

8. A compound of formula (V) R1-SO—S—R2 chosen from the group consisting of thiosulfinates 29, 30 and 33

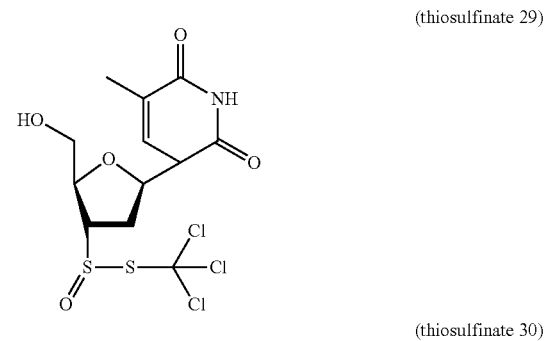

(thiosulfinate 29)

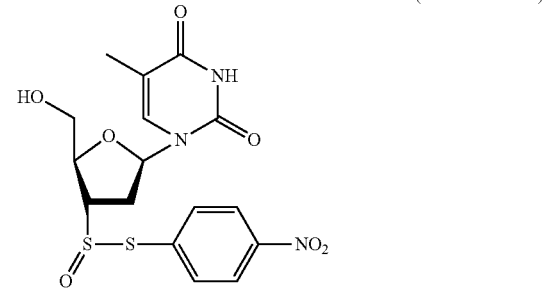

(thiosulfinate 30)

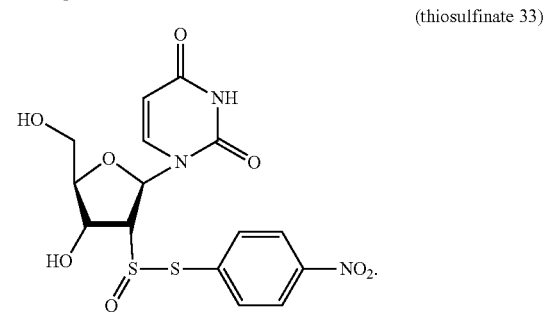

(thiosulfinate 33)

9. A compound of formula (III') R1-S—S—R2' chosen from the group consisting of:
Allyl 3'-deoxythymidin-3'-yl disulfide 37
3'-Deoxythymidin-3'-yl 2-hydroxyethyl disulfide 38
2-Aminoethyl 3'-deoxythymidin-3'-yl disulfide hydrochloride 39
Butyl 3'-deoxythymidin-3'-yl disulfide 40
3-Deoxythymidin-3'-yl hexyl disulfide 41
3'-Deoxythymidin-3'-yl octyl disulfide 42
3'-Deoxythymidin-3'-yl 6-hydroxyhexyl disulfide 43.

10. A compound of formula (VI), R1-S—S—R1 chosen from the group consisting of:
Bis(5-bromo-2',3'-dideoxyuridin-3'-yl) disulfide 36
Bis(2',3'-didehydro-2',3'-dideoxyuridin-2'-yl) disulfide 45.

* * * * *